(12) United States Patent
Ichihara et al.

(10) Patent No.: US 9,097,619 B2
(45) Date of Patent: Aug. 4, 2015

(54) SPECIMEN SLICING GUIDE

(75) Inventors: Shu Ichihara, Nagoya (JP); Mina Yamashita, Anjo (JP)

(73) Assignee: Shu Ichihara, Nagoya-shi (JP)

(*) Notice: Subject to any disclaimer, the term of this patent is extended or adjusted under 35 U.S.C. 154(b) by 410 days.

(21) Appl. No.: 13/457,390

(22) Filed: Apr. 26, 2012

(65) Prior Publication Data

US 2012/0272801 A1 Nov. 1, 2012

(30) Foreign Application Priority Data

Apr. 27, 2011 (JP) .................. 2011-100226

(51) Int. Cl.
*B26D 1/00* (2006.01)
*G01N 1/06* (2006.01)

(52) U.S. Cl.
CPC .. *G01N 1/06* (2013.01); *B26D 1/00* (2013.01); *Y10T 83/0481* (2015.04); *Y10T 83/8878* (2015.04)

(58) Field of Classification Search
USPC ........... 83/130, 466.1, 144, 522.19, 763, 827, 83/468.1, 467.1, 821, 829; 30/293, 114, 30/115, 117, 116; 269/87.2, 54.1
See application file for complete search history.

(56) References Cited

U.S. PATENT DOCUMENTS

| | | | |
|---|---|---|---|
| 1,517,931 A | 12/1924 | Wilbe | |
| 1,626,922 A | 5/1927 | Downs | |
| 1,703,154 A | 2/1929 | Lanzkron | |
| 1,823,608 A | 9/1931 | Kalkanis | |
| D168,127 S | 11/1952 | Schoenfeld | |
| D169,827 S | 6/1953 | Schoenfeld | |
| 3,234,834 A * | 2/1966 | Maurer | 83/130 |
| 3,257,884 A | 6/1966 | Best et al. | |
| 4,773,418 A * | 9/1988 | Hettich | 606/132 |
| 5,148,729 A | 9/1992 | Krumdieck | |
| 6,722,241 B1 | 4/2004 | Anayas | |
| 6,748,839 B2 * | 6/2004 | Whiteman et al. | 83/698.91 |

(Continued)

FOREIGN PATENT DOCUMENTS

| | | |
|---|---|---|
| CA | 506563 | 10/1954 |
| DE | 493712 | 2/1930 |

(Continued)

OTHER PUBLICATIONS

Communication mailed Oct. 30, 2013 from the European Patent Office in counterpart EP application No. 12165773, including European Search Opinion, Search Report and examined claims 1-15.

(Continued)

*Primary Examiner* — Omar Flores Sanchez
(74) *Attorney, Agent, or Firm* — J-Tek Law PLLC; Jeffrey D. Tekanic; Scott T. Wakeman

(57) ABSTRACT

A specimen slicing guide is provided for assisting in slicing a specimen taken from a human or an animal. The specimen slicing guide includes a base extending in a direction having a horizontal component. A plurality of needles extend from the base with gaps provided between the needles in the extension direction of the base. The needles extend at least substantially parallel to each other and at least substantially perpendicular to the horizontal component of base. A needle spacer has a plurality of holes and the plurality of needles are respectively disposed in the plurality of holes. The needle spacer is configured to press against the specimen and to move relative to the base.

20 Claims, 11 Drawing Sheets

(56) References Cited

U.S. PATENT DOCUMENTS

| | | |
|---|---|---|
| 7,219,884 B2 | 5/2007 | Morales |
| 8,191,453 B2 | 6/2012 | Ichihara |
| 2004/0175820 A1 | 9/2004 | Shigematsu et al. |
| 2009/0293689 A1 | 12/2009 | Ichihara |
| 2010/0050838 A1 | 3/2010 | Noguchi et al. |
| 2010/0076473 A1 | 3/2010 | Tawfik et al. |

FOREIGN PATENT DOCUMENTS

| | | |
|---|---|---|
| EP | 2128594 A2 | 12/2009 |
| FR | 1.030.314 | 6/1953 |
| JP | H4-2941 | 1/1992 |
| JP | H5-285887 | 11/1993 |
| JP | H11-207692 | 8/1999 |
| JP | 2006-038466 A | 2/2006 |
| JP | 4392457 B2 | 1/2010 |
| WO | 96/08208 A1 | 3/1996 |
| WO | 00/37918 A2 | 6/2000 |
| WO | 02/088668 A1 | 11/2002 |
| WO | 2004/030516 A2 | 4/2004 |
| WO | 2008/053916 A1 | 5/2008 |
| WO | 2010036931 A1 | 4/2010 |

OTHER PUBLICATIONS

Rosai J., Rosai and Ackerman's Surgical Pathology, 2004, pp. 25-37, Ninth Edition, Mosby, Edinburgh.

* cited by examiner

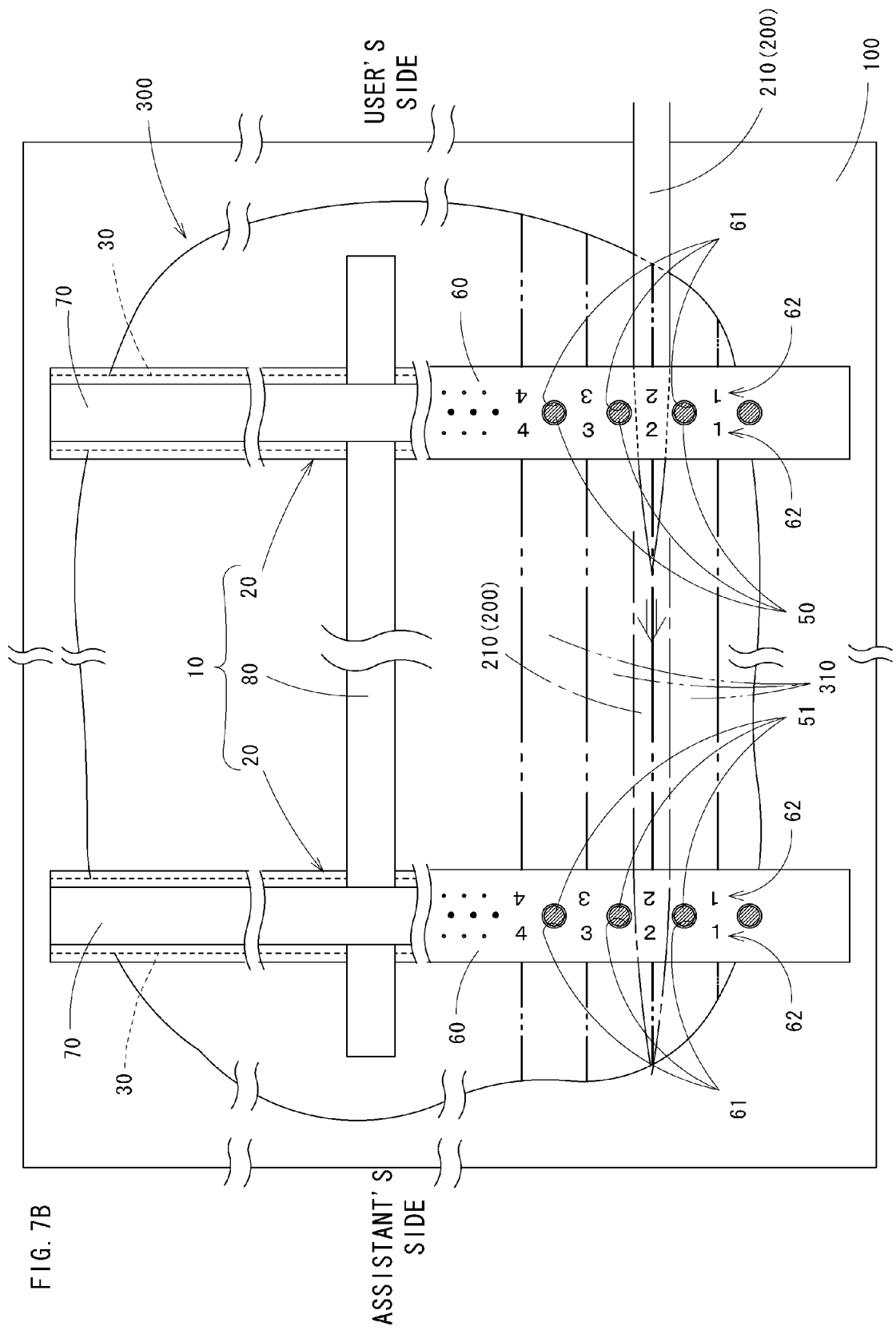

SPECIMEN SLICING GUIDE

CROSS-REFERENCE

This application claims priority to Japanese patent application No. 2011-100226, filed on Apr. 27, 2011, the contents of which are fully incorporated herein by reference.

TECHNICAL FIELD

The present invention relates to a specimen slicing guide, a specimen slicing apparatus and a method of using the same, e.g., to slice a biopsy specimen taken from a human or an animal patient.

BACKGROUND ART

Pathological examinations are conducted on organ or tissue specimens obtained from a human or animal patient, e.g., by performing a biopsy or a surgical operation, for research purposes and to diagnose diseases. A pathological examination generally includes, but is not limited to, the steps of cutting the biopsy specimen into slices or sections and then visually observing the slices (pathological specimens) using a microscope or other imaging apparatus. In more detail, the biopsy specimen may be processed, e.g., by first cutting it by hand with a knife into one or more slices, treating one or more of the slices with alcohol, xylene or other solvents, embedding the treated slice(s) in paraffin and then cutting the slice(s) again using a microtome into one or more thinner slices, usually transparently thin slices. The thinner slices may optionally be stained with a dye such as hematoxylin-eosin (H&E stain) prior to the visual observation step.

For example, when a pathological examination is performed for the purpose of detecting and/or diagnosing the stage of stomach cancer (neoplasm), all or a part of the stomach is surgically excised, the specimen is cut into one or more slices, the slice(s) is/are stained and the stained pathological specimen(s) is/are examined by the surgeon, a pathologist and/or another technician. Additional steps, e.g. such as but not limited to the steps noted above, may also be performed during the pathological examination.

This pathological examination procedure enables a determination of whether cancer (neoplasm) is present, what type of neoplasm is present (e.g., benign or malignant), how far the cancer has spread (including the condition of the margin of the specimen), the stage of the cancer, whether there is any vascular invasion, etc.

Herein, the phrase "the margin of the specimen" means the end of the biopsy specimen along the cut that was made to excise the tissue or organ from the patient.

Information about the interior of the specimen is also important in order to accurately diagnose the condition of the margin. If the condition of the margin and the condition of the interior are both accurately diagnosed, the spread of stomach cancer or other disease under investigation can be diagnosed more precisely.

It is often desirable to prepare a plurality of uniformly thin slices from the biopsy specimen. In this regard, it may be desirable that each individual slice or segment has a uniform thickness across its entire cross section, e.g., width. In addition, it also may be desirable in certain investigations that all slices or sections have the same uniform thickness.

Conventionally, the pathologist, a technician or another person skilled in slicing tissue samples (hereinafter, collectively, the "pathologist, etc." or "the user") would prepare the tissue samples by holding the biopsy specimen with one hand (such as the left hand) while slicing or cutting the biopsy specimen using a knife in the other hand (such as the right hand). Thus, in the past, the user has been required to use only his or her eyesight and manual dexterity in order to prepare tissue slices having uniform thickness.

Consequently, such a conventional tissue sample preparation technique suffers from the problem that it is highly dependent on the cutting skill of the user such that undesirable variations in tissue sample thickness often occur.

Japanese Patent Application Laid-Open No. 2009-288169 and its corresponding US Patent Publication No. 2009-0293689 A1 propose a specimen slicing apparatus designed to overcome these problems of the prior art. This specimen slicing apparatus includes a pair of specimen sliding guides slidably coupled by a link so as to be spaced apart in a parallel relationship. The needles of the specimen slicing guides are adapted to pierce through a specimen into a support surface and to hold the specimen for slicing. The slicing work is performed by inserting a knife into the corresponding gaps between two adjacent needles in the two specimen slicing guides and downwardly cutting through the specimen using the adjacent needles as a guide for the knife, thereby enabling the reliable preparation of uniform specimen slices that does not depend particularly on the skill of the user.

SUMMARY OF THE INVENTION

While this known specimen slicing guide and apparatus provide a significant advance and improvement over known slicing techniques, further improvements are possible. For example, it has been found that, when the needles of the specimen slicing guides are pressed against the specimen in order to pierce the specimen and stick into the support surface, the needles are subjected to an impact force that can cause the metal needles to permanently bend (plastic deformation) in the lateral direction. Even though the metal needles are resiliently bendable (elastic) to a certain degree, the amount of force necessary to pierce a tough specimen may exceed the elastic deformation limit of the needle. Thus, one or more needles may no longer be straight after the specimen slicing guide is used to slice a tough specimen.

Moreover, if the needles are subjected to repeated plastic deformations of this nature over an extended period of time, one or more needles may become permanently misaligned, i.e. they will no longer extend parallel to each other. That is, the gaps between adjacent needles may gradually widen or narrow from the proximal end (the base side) toward the distal end in an undesired manner. If this happens, it may become difficult or impossible to cut the specimen into uniform slices using the specimen slicing apparatus.

Also, after the specimen slicing guide has been used to slice a specimen, it is often not easy to separate the specimen slicing guide from the specimen (i.e. the specimen slices) and/or the support surface (that is, to pull the needles out of the specimen and/or the support). For example, if the needles are snugly pierced into the specimen (slices) and/or the support surface, a frictional force is exerted between the needles and the specimen (slices) and/or the support surface when the specimen slicing guide (the needles) is raised to withdraw the needles from the specimen (slices) and the support surface. In this case, the specimen (slices) may be lifted with the needles and thus the needles do not easily separate from the specimen (slices) after the slicing operation has been completed.

Therefore, it is an object of the present teachings to disclose a further improved specimen slicing guide, specimen slicing apparatus and method for slicing a specimen.

According to one aspect of the present teachings, a specimen slicing guide is preferably configured to assist in slicing a specimen taken from a human or an animal. The specimen slicing guide preferably includes a base extending in a direction having a horizontal component. A plurality of needles preferably extends from the base in a spaced relationship, such that gaps are defined between the respective needles in the extension direction of the base, e.g., in the horizontal direction of the base. The needles preferably extend at least substantially parallel to each other and at least substantially perpendicular to the horizontal component of base. Further, a needle spacer preferably has a plurality of holes. In this case, the plurality of needles may be respectively disposed in the plurality of holes. The needle spacer is preferably configured to be pressed against the specimen and to move relative to the base along the lengthwise direction of the needles.

According to this aspect of the present teachings, the plurality of needles may be held more reliably in a parallel relationship so that specimens can be properly sliced over an extended period of usage, i.e. plastic deformation of the distal ends of the needles may be reliably minimized and/or prevented. In addition or in the alternative, the needles can be more easily separated from the specimen (slices) after the specimen slicing operation. These advantages will be further discussed in detail below.

According to another aspect of the present teachings, the plurality of needles provided on (extending from) the base may be spaced apart equidistantly in the extension (e.g., horizontal) direction of the base and may extend downward substantially vertically from the base (e.g., perpendicularly or substantially perpendicularly).

According to another aspect of the present teachings, a paired set of specimen slicing guides may be used in the following manner. After the specimen has been placed on a support surface, the pair of specimen slicing guides are aligned so as to mutually oppose each other, e.g., in a substantially parallel relationship. The two specimen slicing guides are then lowered from above the specimen toward the specimen, so that one or more of the needles of each specimen slicing guide pierce the specimen, penetrate through the specimen and stick into the support surface. As a result, the pair of specimen slicing guides will be supported by the support surface. In this manner, the specimen can be easily fixed at a specific location on the support surface, and the specimen slicing guides themselves are also fixed at the specified locations. This procedure will be referred to hereinbelow as the "set up" of the specimen slicing guide(s). Naturally, the two slicing guides may both be set up at the same time, or may be set up one at a time, i.e. sequentially.

When the slicing guides (slicing assisting tools) have been set up as described above, the user then inserts the blade of a knife into the space formed by the gap between two adjacent needles of one slicing guide and the corresponding (mutually opposing) gap between two adjacent needles of the other slicing guide (this may be referred below to as a "paired gap formation space"). The knife is then lowered along this paired gap formation space (that is, while being guided by the two pairs of needles forming the paired gap formation space), thereby cutting the specimen and forming a specimen slice. The specimen can be uniformly sliced by continuing to perform the above-mentioned cutting or slicing work in adjacent paired gap formation spaces. That is, the slice thickness can be kept the same at each location of the slice (uniform in the broad sense). Naturally, specimen slices having different thicknesses may be prepared by selecting different paired gap formation spaces to downwardly guide the knife blade, i.e. a specimen slice may have a width equal to two or more needle gap widths.

Needle spacer(s) according to the present teachings may be used in the following manner. While a single needle spacer may be used with a single specimen slicing guide to slice a specimen in accordance with the present teachings, the following description will describe a paired set of specimen slicing guides that collectively form a specimen slicing apparatus.

First, the needle spacers are respectively positioned at or near the distal ends of the plurality of needles of the two specimen slicing guides. The needles are then lowered towards the specimen as described above. While the needles are piercing the specimen and penetrating through the specimen (e.g., during all or only a portion of the set up process), the needle spacers preferably contact the upper surface of the specimen. As a result, the needle spacers will move (upward) relative to the needles as the specimen slicing guides are pressed downwardly to fix the specimen guides and the specimen to the support surface. That is, the needle spacers may generally be held stationary on, at or near the upper surface of the specimen, such that the needle spacers will move closer to the respective bases.

Therefore, while the needles are piercing the specimen and passing through the specimen (again, during all or only a portion of the set up process), the respective portions of the plurality of needles located at or near the upper surface of the specimen are held or retained in the spaced relationship of the holes of the needle spacers. That is, this portion of the needles is constrained to the spacing that corresponds to the spacing of the holes in the needle spacers. As a result, when the needles pierce the specimen and pass through the specimen into the support surface, the needle spacer prevents the needles from bending laterally (i.e. perpendicular to the extension or lengthwise direction of the needles) due to the impact force caused by striking the specimen, passing through the specimen (especially if the middle of the specimen includes a difficult-to-penetrate layer) and/or the support surface. Therefore, the needles are maintained parallel to each other throughout the set up process and the specimen slicing guide is thus capable of reliably serving as a guide for uniformly slicing specimens over an extended period of usage. That is, undesirable plastic (permanent) deformation of the needles can be minimized or prevented.

The needle spacer may be held in contact with the upper surface of the specimen (or substantially adjacent thereto) by gravity during the set up procedure. In the alternative, the user (or an assistant thereto) may manually hold the needle spacer in a stationary position relative to the upper surface of the specimen during at least a portion of the set up process. Of course, it is also possible to provide a separate mechanical (retaining) device, such as a clamp, to hold the needle spacer in a stationary position (i.e. without the need for a human to do so) while the specimen slicing guides are being inserted through the specimen into the support surface.

After the specimen slicing guides have been set up as described above, the needle spacers are then preferably moved up and away from the upper surface of the specimen, so that the user can insert a knife into a gap between the appropriate set of needles and slice the specimen without interference from the needle spacers. That is, during the slicing operation, the needle spacers are preferably held at a position where the knife blade is lower than the needle spacers, and at a position high enough so that it is possible to insert the knife into the specific paired gap formation spaces without interfering with the needle spacers.

In another aspect of the present teachings, the specimen slicing guide(s) preferably further include(s) a manipulation member that is disposed above, e.g., extends along, an upper side of the base, i.e. on the side of the base that is opposite of the needle spacer. In addition, at least one linking bar preferably extends through, and is slidable relative to, the base. In this case, a first end of the linking bar is connected or affixed to the manipulation member and a second end of the linking bar is connected or affixed to the needle spacer, such that the base is disposed between the manipulation member and the needle spacer with the at least one linking bar connecting the manipulation member and the needle spacer.

The manipulation member is preferably in the form of a handle, but also may be a knob or other structure that can be grasped by the human hand in order to move it. Also, while the manipulation member is embodied as a generally flat or straight bar in the preferred embodiment, the shape of the manipulation member is not particularly limited as long as it can be manipulated or manually operated to move the needle spacer relative to the base. For example, the manipulation member may include a curved or stepped portion.

In a preferred embodiment, at least first and second linking bars extend through the base and connect the manipulation member to the needle spacer. For example, the first and second linking bars may extend in parallel to the plurality of needles with the plurality of needles being disposed therebetween. It should be understand that the linking bar(s) need not extend through a hole in the base that entirely surrounds the linking bar, but also may be movably disposed in a groove or channel that only partially encloses the linking bar. Furthermore, the linking bar could be disposed entirely outside of the base. For example, the bar may include an outwardly-projecting tongue disposed on its outer axial end and the linking bar may include a channel or groove having an inner contour or profile shaped to correspond or conform to the tongue. In this case, the linking bar may be movably connected to the base such that the linking bar is slidable relative to the base by relative sliding along the tongue and groove/channel arrangement.

In this aspect of the present teachings, the specimen slicing guide(s) can be used in the following manner. After the specimen has been sliced and it is desired to remove the specimen slicing guide(s), the needle spacer(s) may be moved downwardly relative to the base(s) so as to contact the upper surface of the specimen (e.g., after it has been sliced). Then, the manipulation member may be pressed downwardly while the base is urged or moved upwardly. In this case, a pressing (compressive) force is transmitted from the manipulating member via the linking bar(s) to the needle spacer, thereby causing the needle spacer to press downwardly against the specimen. This downward pressing force prevents the specimen and the support surface from rising when the base is urged or moved upwardly. However, the needles will rise together with the base. Therefore, the specimen and the support surface will be prevented from rising, even though the needles are rising against the frictional force acting between the needles and the specimen and/or support surface (alternatively, it is understood that the needle spacer(s) will be descending relative to the needles). Consequently, the specimen slicing guide can be easily separated from the specimen and the support surface.

That is, the needles will be removed from the specimen and the support surface when the needle spacer reaches its lowermost or farthest-most position relative to the base (or near the lowermost position or farthest-most position). More specifically, when the distal ends of the needles reach the same height as the lower edge of the needle spacers (the same height as the upper surface of the specimen), the needles will have been pulled out of the specimen so that the specimen slicing guide can be easily separated from the specimen and the support surface.

In another aspect of the present teachings, the needle spacer is configured or adapted to be moved to a needle tip inclusion position. At this position, the distal ends (i.e. including the tips thereof) of the plurality of needles are preferably located between upper and lower edges of the needle spacer. More preferably, the needle tip inclusion portion includes the lowermost position, to which the needle spacer is movable away from the base. In this case, when the needle spacer is disposed such that the needle tips are located or disposed within the needle tip inclusion portion, the sharp points or edges of the needles will be enclosed within the needle spacer, thereby preventing the shape needle tips from causing injury to the user or the assistant.

Such a specimen slicing guide may be used in the following manner. First, the needle spacers are positioned at the needle tip inclusion position and the needle spacer is placed onto the upper surface of the specimen. In this state, the needles are lowered toward the specimen so as to pierce and pass through the specimen and then still further into the support surface while the needle spacers continuously contact the upper surface of the specimen. As a result, the needle spacers will move upward relative to the needles, i.e. the needle spacers will move towards the base.

Thus, during the entire process of fixing the specimen slicing guide(s) to the specimen and to the support surface (i.e. during the "set up"), it is possible to prevent the sharp needle tips from contacting anything other than the specimen and the support, thereby improving safety during the set up process. Furthermore, by maintaining the sharp distal ends of the needles within the needle spacer (i.e. within the needle tip inclusion space) when the specimen slicing guide(s) is (are) not in use, there will be no time when the sharp distal ends of the needle will be exposed, thereby further improving safety.

Preferably, the specimen slicing guide is configured so that the needle spacers can only descend to the needle tip inclusion position as their lowermost position (i.e. the farthest position of the needle spacer from the base). Therefore, the needle spacers are prevented from separating or being removed from the needles and thus from the specimen slicing guide. This design provides the following two advantages. First, because the needle spacer can not be removed from the base and needles, it can not be lost. Second, it is also not necessary to thread the set of needles through the corresponding set of holes in the needle spacer, which would be necessary if the needle spacer could be removed from the needles.

Therefore, in another aspect of the present teachings, when the needle spacer descends (moves) to the needle tip inclusion position, the needle spacer preferably does not require any additional means for preventing the needles from coming out of the needle spacer. Therefore, the needle spacer can be easily lowered to the needle tip inclusion position without a concern that the needle spacer might come off of the needles.

Thus, as a representative example of this aspect of the present teachings, the manipulation member is preferably configured or adapted to abut on the base when the needle spacer is disposed in its lowermost position. In such an embodiment, the length of the linking bar(s) is (are) selected so that the needle spacer will be located at its lowermost position (farthest-most position from the base) when the manipulation member abuts the base. Because the contact of the manipulation member on the base prevents further downward movement of the needle spacer, this allows the lowermost position of the needle spacers to be reached without a concern that the needle spacer will come off the needles. Furthermore, the user will know that the sharp distal ends of the needles are located within the body of the needle spacer (the needle tip inclusion position) and the specimen slicing guide can be moved without fear of injury.

In another aspect of the present teachings, at least one insertion hole is defined in the base and is sized to receive a human finger or thumb therein. As was described above, after the slicing work is performed using the specimen slicing guide, the manipulation member may be pressed downward while the base is urged upward to separate the specimen slicing guide from the specimen and the support surface. The at least one insertion hole can facilitate this separating operation, because the user can insert a finger or thumb into the at least one insertion hole defined in the base in order to more easily urge the base upwardly and/or to move the base closer to the manipulation member. At the same time, the other finger(s) and/or thumb of the same hand may be used to press the manipulation member downwardly and/or to move the manipulation member closer to the base.

In another aspect of the present teachings, the specimen slicing guide preferably includes a fixing mechanism configured or adapted to releasably fix the needle spacer relative to the needles in order to prevent movement of the needle spacer along the lengthwise direction of the needles relative to the base. The fixing mechanism preferably enables the needle spacer to be releasably fixed at any height or location along the length of the needles between the base and the distal ends of the needles.

In such an embodiment, when it is desired to fix or fasten the needle spacer at a specific position along the length of the needles, the fixing mechanism may be manipulated by the user to change the needle spacer from being in a movable (unlocked) state into an immovable (locked) state, thereby reliably maintaining the needle spacer at a desired position.

In another aspect of the present teachings, the fixing mechanism may include at least one threaded hole disposed in the base adjacent to the linking bar(s), and at least one screw threadably disposed in the at least one threaded hole. The at least one screw is preferably configured or adapted to move between a pressing (fixing) position, in which the screw is pressed against the linking bar, and a non-pressing (free movement) position, in which the screw is not pressed against the linking bars.

In a preferred embodiment, a first threaded hole may be disposed adjacent to a first linking bar and a second threaded hole may be disposed adjacent to a second linking bar. A screw is disposed in each of the first and second threaded holes and is configured to contact and press against the corresponding linking bar to fix the position of the needle spacer relative to the base.

In such an embodiment, when the screw(s) is (are) loosened and thus is (are) located at the non-pressing position (e.g., the terminal end of the screw(s) does (do) not abut and/or press against a lateral side of the adjacent linking bar(s)), the needle spacer is permitted to freely move in the lengthwise direction of the plurality of needles. On the other hand, when the screw(s) has (have) been tightened and is (are) located at a pressing position (e.g., the terminal end of the screw(s) abut(s) and press(es) against the lateral side of the adjacent linking bar(s)), the needle spacer is prevented (or locked) from moving in the lengthwise direction of the plurality of needles, and thus is maintained (fixed) at that height position.

Although the fixing mechanism of the preferred embodiment utilizes a screw and threaded hole, the present teachings are not particularly limited in this regard. For example, the linking bar(s) may include a plurality of laterally-extending (i.e. perpendicular to the lengthwise direction of the linking bar(s)) holes. In this case, a removable pin may be provided that can be inserted through a particular hole in the linking bar to lock the linking bar at a particular position relative to the base.

In the alternative, the linking bar(s) and base may include a ratchet mechanism configured or adapted to releasably fix the linking bar(s) at a plurality of positions relative to the base.

It should be understood that, in embodiments comprising two or more linking bars that connect the manipulating member to the needle spacer, only one fixing mechanism may be provided, although the preferred embodiment below provides one fixing mechanism per linking bar.

In another aspect of the present teachings, gap identification markers may be provided on the needle spacer so as to identify one or more respective gaps between adjacent needles.

In such an embodiment, after a pair of specimen slicing guides have been set up as described above, the user can use the gap identification markers as a visual reference when inserting the blade of the knife into a specific paired gap formation space in order to slice the specimen. By utilizing corresponding gap identification markers on a pair of spaced-apart specimen slicing guides as a visual guide, the slicing work can be facilitated. That is, the visual references make it easier for the user to insert the knife blade into the correct corresponding gaps between specific adjacent needles of the two specimen slicing guides. Thus, the user can more quickly and accurately cut the specimen into uniform slices or into slices having any desired width, in case slices of different widths are desired.

Also, by providing the gap identification markers on the needle spacer in such a specimen slicing guide, the following advantages result as compared to providing the gap identification markers on the base. Specifically, because the plurality of needles extend at least substantially vertically downward from the base, and the needle spacer is movable along the lengthwise direction of the needles, the needle spacer (and thus the gap identification markers thereof) is located lower than the base and thus closer to the specimen. As a result, the gap identification numbers will be disposed closer to the specimen (than if the gap identification numbers are located on the base) and the user can more easily find the correct gap(s) between adjacent needles to insert the blade of the knife. Consequently, the specimen can be more reliably sliced into the desired width(s) than when gap identification markers are provided on the base as a visual guide.

Also, since the needle spacers can move in the lengthwise direction of the needles according to such a specimen slicing guide, the following results. That is, after the pair of specimen slicing guides have been set up as above and the user intends to insert the knife blade into a particular gap or into a particular pair of mutually opposing gaps on a pair of specimen slicing guides, the needle spacer must be maintained at a position that is sufficiently higher than the specimen However, this means that the needle spacer must be maintained at a position that is high enough to allow insertion into the gap(s) with the knife blade lower than the needle spacer so that the needle spacer does not interfere with the specimen, as was discussed above.

Therefore, if the needle spacer is maintained at a position that is as low as possible while still satisfying this condition, the needle spacer (the gap identification markers thereof) will be located at a position that is closer to the specimen. Because of this, the blade of the knife can be inserted into the gap(s)

between adjacent needles even more easily, and the specimen can be uniformly sliced even more easily, than when gap identification markers are provided on the base as a guide.

In another aspect of the present teachings, the gap identification markers may be provided on both sides in a width direction of the needle spacer.

In such an embodiment, because the gap identification markers are provided in both directions in the width direction of the needle spacer, the plurality of holes in the needle spacer may serve as a visual reference. The side with the plurality of holes is defined as the upper side. In this case, after a pair of these specimen slicing guides have been set up as described above and the user inserts the blade of a knife into a corresponding set of mutually opening gaps, the user will be located on one side of the pair of specimen slicing guides. Therefore, the gap identification markers located on the user's (i.e. the person holding the slicing knife) side of the needle spacer of one specimen slicing guide serve as the user's visual guide. However, an assistant to the user may be located on the other side of the pair of specimen slicing guides, i.e. on the opposite side from the user with the pair of specimen slicing guides in between them. Therefore, the assistant can use the gap identification markers on the assistant's side of the needle spacer of the other specimen slicing guide as a visual guide to advise the user whether the knife blade has been inserted into the correct needle gap, thereby facilitating a uniform and accurate slicing of the specimen.

In another aspect of the present teachings, a specimen slicing guide apparatus may include two specimen slicing guides according to any preceding or following embodiments and a link configured or adapted to adjustably retain the two specimen slicing guides in a spaced-apart, parallel relationship.

In such an embodiment, a single specimen slicing guide apparatus is formed by linking a pair of specimen slicing guides a mutually-opposing, parallel state. Therefore, the pair of specimen slicing guides can be easily set up in a mutually opposing (parallel) state by lowering the entire specimen slicing guide apparatus all at once from above the specimen and toward the specimen. Thus, the pre-slicing preparation for fixing the specimen to the support surface can be easily carried out using this specimen slicing guide apparatus.

In further aspects of the present teachings, the needles may be equally spaced apart in a linear row at intervals between 2-4 millimeters. In addition or in the alternative, the needles may be resiliently bendable. In addition or in the alternative, the needles may have a rounded outer profile corresponding to an inner cross section of the holes of the needle spacer. And, in addition or in the alternative, the needle spacer may have a flat side configured to abut against the specimen. More preferably, the needle spacer may be polygonal or semi-circular shaped with a flat side facing the specimen, such as rectangular shaped.

In another aspect of the present teachings, a method for slicing a specimen taken from a human or an animal may include placing the needle spacer of any specimen slicing guide described above or below on an upper surface of the specimen. Then, at least some of the needles of the specimen slicing guide are pushed through the specimen and into a support surface while the needle spacer is maintained at or near the upper surface of the specimen, thereby fixing the needles in the support surface relative to the specimen. The specimen is then sliced using gaps between adjacent needles as a guide for a knife. Subsequently, the needles are removed from the sliced specimen by upwardly moving the needles away from the sliced specimen and support surface while the needle spacer is maintained at the upper surface of the specimen.

In another aspect of the present teachings, the needle spacer may be maintained at or near the upper surface of the specimen by pressing down on a manipulation member connected to the needle spacer via at least one linking bar. In addition or in the alternative, after the pushing step but before the slicing step, the needle spacer may be moved away (e.g., upwardly) from the specimen and the needle spacer may be releasably fixed relative to the needles, e.g., using a fixing mechanism.

Further objects, aspects, embodiments, advantages and uses of the present teachings will become apparent after reviewing the following detailed description of embodiments of the present invention in conjunction with the appended drawings and claims.

BRIEF DESCRIPTION OF THE DRAWINGS

FIG. 7B is a detailed plan view (partially cut away) for illustrating a method of using (slicing method) the specimen slicing guide apparatus of FIG. 1.

DESCRIPTION OF THE PREFERRED EMBODIMENTS

Figure 1:
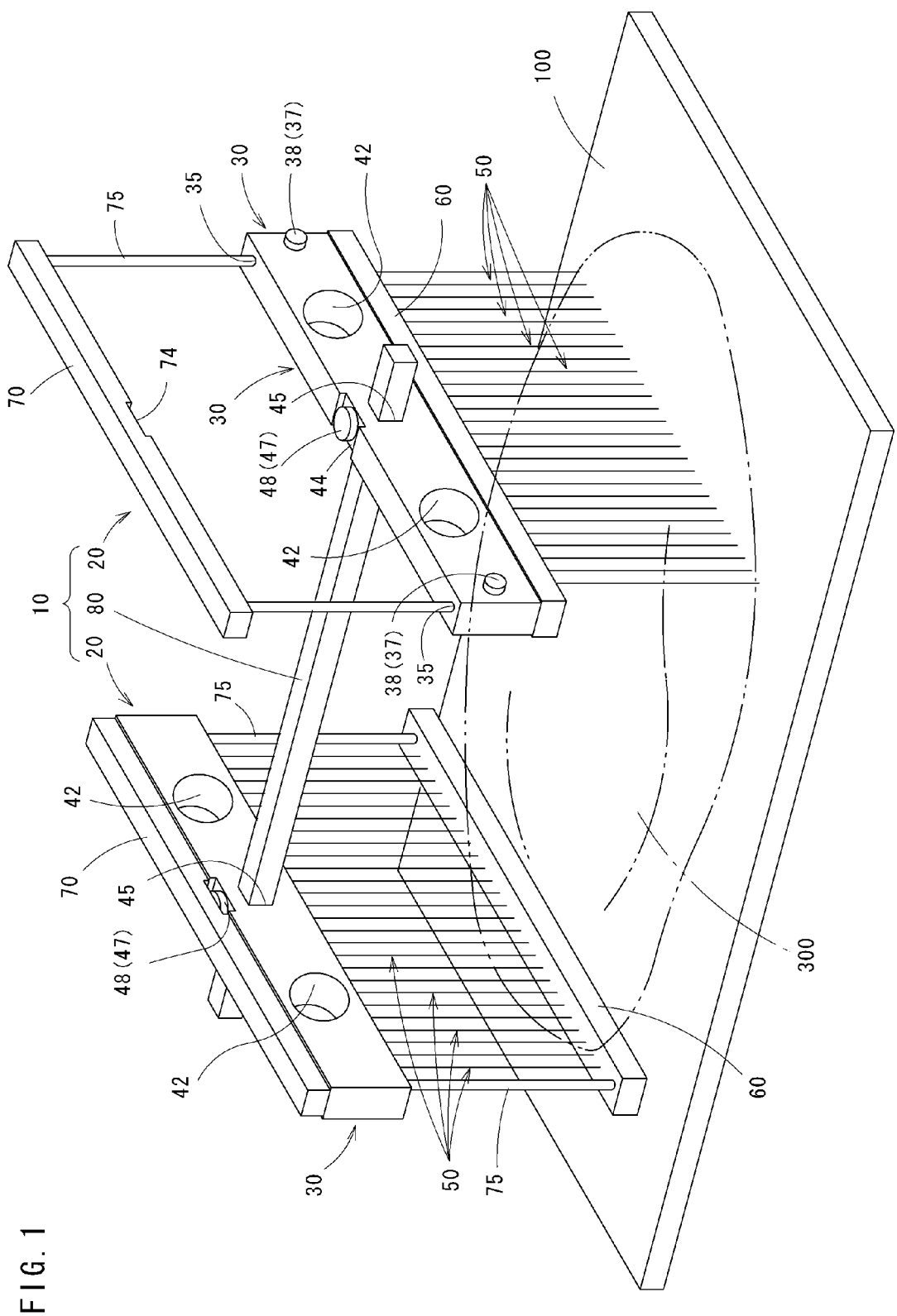
FIG. 1 is a perspective view of a specimen slicing apparatus according to an exemplary embodiment of the present teachings, wherein the distance between the two specimen slicing guides has been widened; for explanatory purposes, the needle spacer (left side of FIG. 1) of one specimen slicing guide is located at its lowermost position (needle tip inclusion position) relative to the base and the needle spacer (right side of FIG. 1) of the other specimen slicing guide is located at its uppermost position relative to the base.

Representative, non-limiting examples of the present invention will now be described in further detail with reference to the attached drawings. This detailed description is merely intended to teach a person of skill in the art further details for practicing preferred aspects of the present teachings and is not intended to limit the scope of the invention. Furthermore, each of the additional features and teachings disclosed below may be utilized separately or in conjunction with other features and teachings to provide improved specimen slicing guides and specimen slicing apparatus, as well as methods of using the same.

Moreover, combinations of features and steps disclosed in the following detail description may not be necessary to practice the invention in the broadest sense, and are instead taught merely to particularly describe representative examples of the invention. Further, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

Furthermore, the following definitions may be utilized to better understand the scope of the subject matter disclosed herein, as well as the claims.

For example, as used herein, the term "specimen" or "extract" is not limited to the removal of internal organs from a human, animal etc., and also encompasses tissue and other bodily structures that may be removed or extracted from a human, animal, etc., such as skin tissue. The term "specimen" is intended to be equivalent to, and thus encompass, similar terms such as "biopsy specimen", "extract", "sample", etc.

Further, the phrases "extending in a direction having a horizontal component" and "extending downward substantially vertically" herein refer to a specimen slicing guide while it is disposed in its normal usage state, i.e. to cut or slice a specimen disposed on a support surface. "Downward substantially vertically" is understood as encompassing "downward vertically."

In addition, a variety of persons may utilize the specimen slicing guides and specimen slicing apparatus according to the present teachings, such as a pathologist, a doctor, a technician, or any another person skilled at cutting or slicing specimens, etc. Hereinbelow, the person who is cutting (slicing) the specimen (i.e. holding the knife) may be generally referred to as "the user". A person who is assisting the user, but is not handling or controlling the knife or cutting (slicing) the specimen, may be generally referred to "the assistant".

Furthermore, the term "needle spacer" should understood broadly as any device or structure capable of maintaining the spaced relationship (e.g., parallel) of the needles without significant bending while the needles are being pushed into a specimen and/or a support surface. That is, the "needle spacer" according to the present teachings preferably prevents the needles from being laterally bent (i.e. generally perpendicularly to the lengthwise or extension direction of the needles) beyond the elastic deformation limit of the needles, so that the gaps or widths between adjacent needles are prevented from significantly changing over repeated usage of the present specimen slicing guides.

Figure 3:
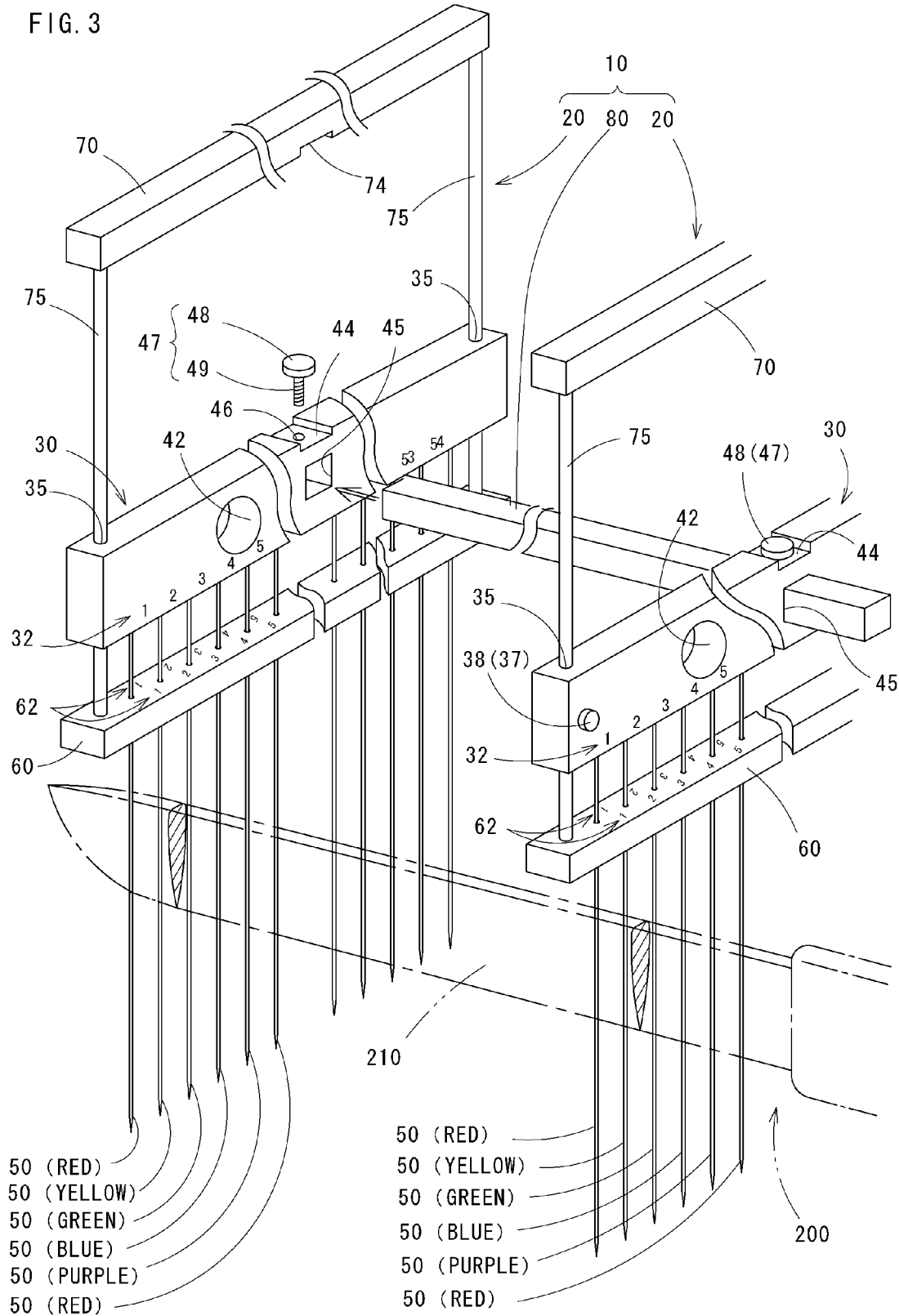
FIG. 3 is a detailed perspective view showing the specimen slicing guide apparatus of FIG. 1.
Figure 7A:
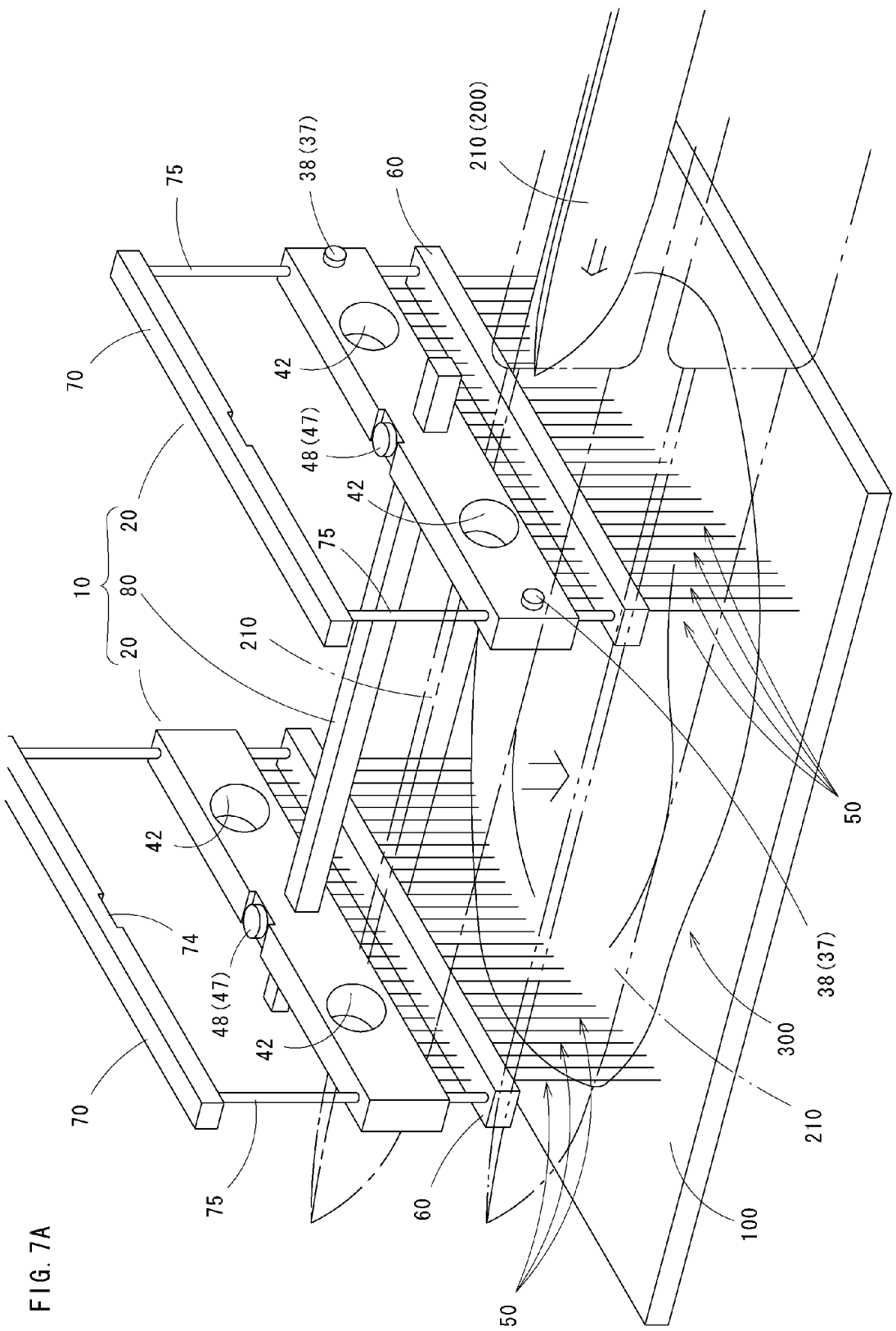
FIG. 7A is perspective view for illustrating a method of using (slicing method) the specimen slicing guide apparatus of FIG. 1.

An exemplary embodiment of the present teachings will now be described with reference to the drawings. As shown in FIGS. 1 and 3, a representative specimen slicing guide apparatus 10 includes a pair of specimen slicing guides 20 and at least one link 80. As shown in FIG. 7A, the specimen slicing guide apparatus 10 (i.e. the two interconnected specimen slicing guides 20) may be used with a support 100 having an upper surface (see FIG. 1 as well) and a knife 200 (see FIG. 3 as well). Hereinbelow, the support upper surface may also be referred to as support surface 100.

As shown in FIGS. 1 to 5, the specimen slicing guides 20 each have a base 30, a plurality of needles 50, a needle spacer 60, and a manipulation member (handle) 70. The guides 20 are symmetrically arranged relative to each other when connected as a specimen slicing apparatus 10.

According to this representative (but not limiting) embodiment, the base 30 is made from a plastic material, e.g., a synthetic resin, and is in the form of a linear bar, although it may be made of other materials (e.g., metal) and have other shapes (e.g., curved, arched or angled). During a specimen slicing operation, the base 30 extends at least substantially horizontally with respect to its lengthwise or extension direction, and extends substantially vertically with respect to its width direction.

As shown in FIGS. 1-4, the needles 50 extend from the base 30. For example, twenty (20) to one hundred (100) needles 50 may extend at least substantially perpendicularly from the base 30, although the number of needles is not particularly limited. The needles 50 may be attached to the base 30 so that they can be replaced individually or in groups in the event of damage. The needles 50 are preferably formed from metal, e.g., from a resiliently bendable metal such as steel (e.g., stainless steel), and preferably extend perpendicularly to the base 30. In addition, the needles 50 preferably extend parallel to each other.

During a normal slicing operation, the needles 50 will extend linearly and at least substantially vertically downward from the base 30. The needles 50 may all have the same shape and size, e.g., they may have a circular cross section over their entire length, although the needles may also have a semi-circular or polygonal cross section. The needles 50 are preferably linearly aligned in a row and spaced equidistantly apart in the lengthwise direction of the base 30. More preferably, the needles 50 are aligned in a row with uniform gaps or spaces between them.

As shown in FIG. 3, the spacing of the needles 50 (more precisely, the width of the gaps between adjacent needles 50) basically corresponds to the thickness of the blade 210 of the knife 200. For example, the needle spacing preferably corresponds to the thickness of the largest portion of the thickness of the blade 210 of the knife 200. The gaps between adjacent needles 50 may be substantially the same as the thickness of the thickest portion of the blade 210, and have a width that is slightly greater than this thickness. For example, the gap between adjacent needles 50 is preferably about 2 to 4 mm.

The base 30 includes identification markers for identifying the needles 50 or the gaps of the needles 50. The identification markers preferably correspond to the needles 50 or to the gaps of the needles 50 (the gaps between adjacent needles 50). Identification markers for identifying the gaps of the needles 50 will be called "gap identification markers" herein, while identification markers for identifying the needles 50 themselves will be called "needle identification markers" herein.

Figure 2:
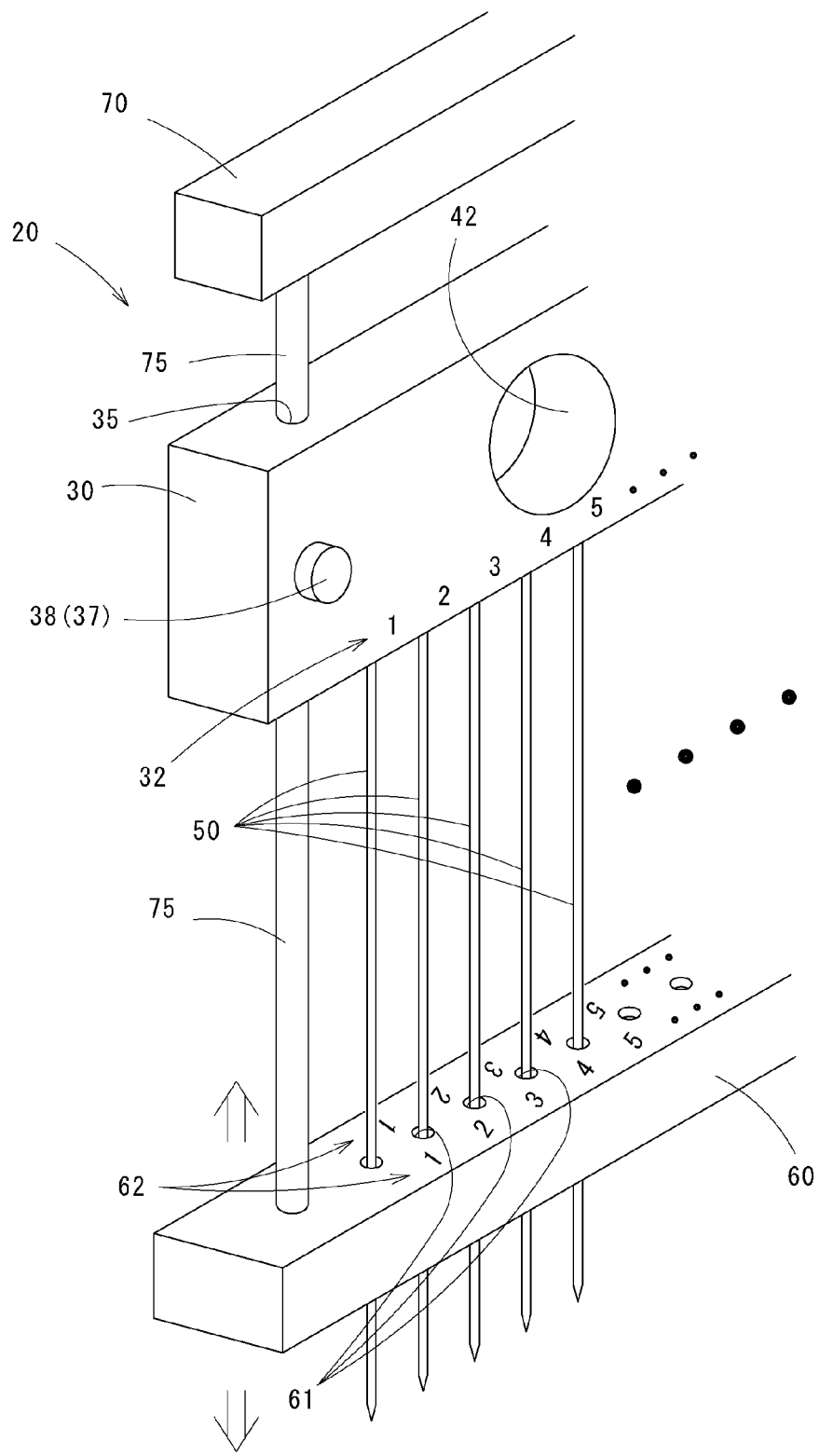
FIG. 2 is a detailed perspective view showing certain components of the specimen slicing guide of FIG. 1.
Figure 4:
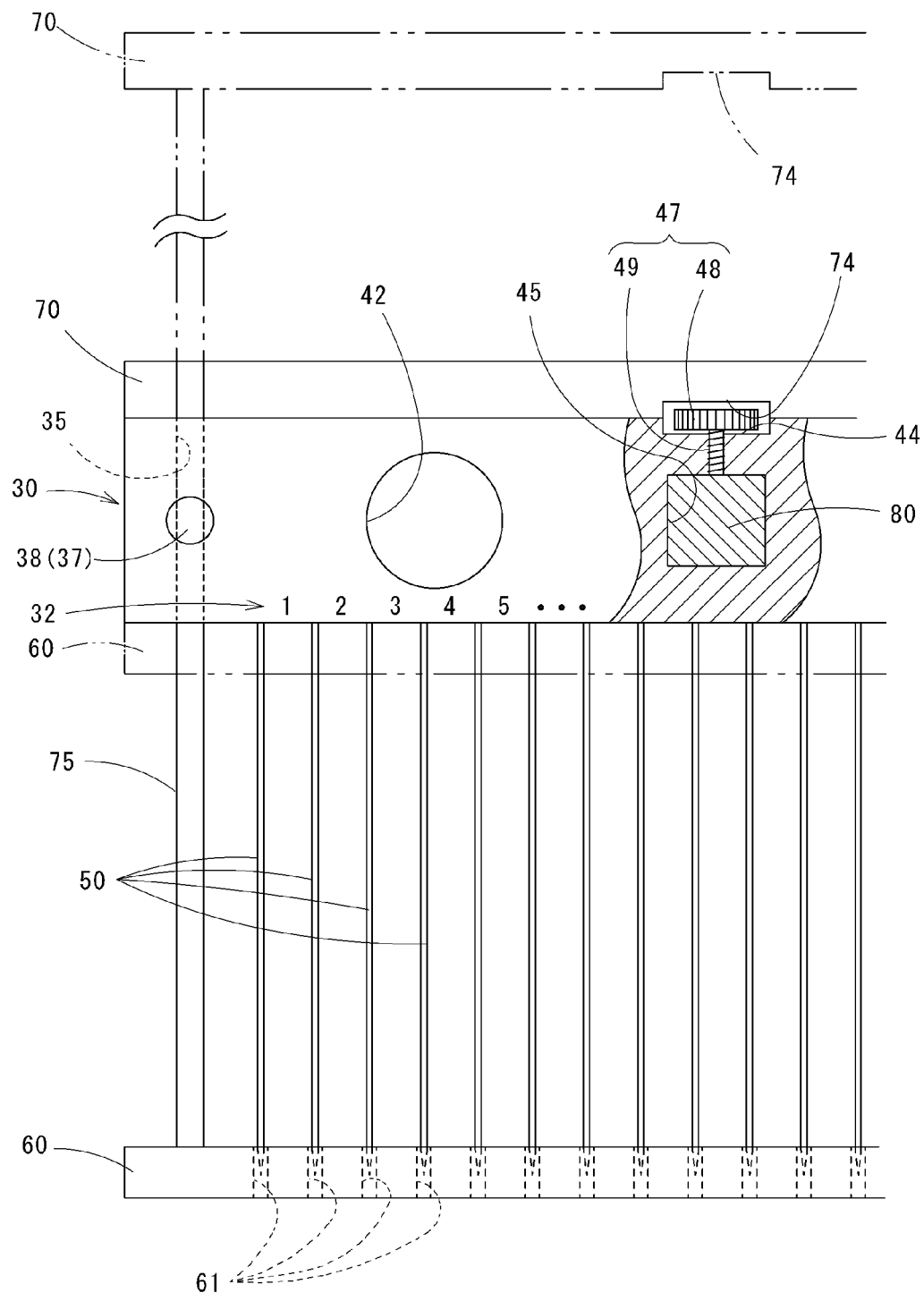
FIG. 4 is a detailed front view (partially cut away) of one specimen slicing guide of FIG. 1, in which the lowermost position (needle tip inclusion position) of the needle spacer is indicated with solid lines, while the uppermost position of the needle spacer is indicated with two-dot chain lines.

As shown in FIGS. 2-4, gap identification markers 32 are provided on the base 30 (not shown in FIG. 1 and FIGS. 6A to 7A for clarity purposes) in this exemplary embodiment and will be called base gap identification markers 32 herein. The gap identification markers 32 may be Arabic numerals (natural numbers), and are assigned to the gaps between the needles 50 (all of the gaps). For example, the numeral "1" is assigned to correspond to the first gap (the gap between the first needle 50 and the second needle 50), the numeral "2" is assigned to correspond to the second gap (the gap between the second needle 50 and the third needle 50), and so forth.

This however is not the only identification option, as the gap identification markers (32) may be assigned to only some of the gaps, such as just the even-numbered gaps, or only to gaps that are multiples of three or more, e.g., five. Naturally, the gap identification markers (32) are not limited to being numerals, and may instead be any kind of symbols, graphics, or the like. The identification markers of any of the embodiments herein may also be represented by different colors, e.g., red, blue, yellow, etc.

Although not depicted in the drawings, needle identification markers may be assigned to the base 30 instead of the gap identification markers 32, or in addition to the gap identification markers 32. Again, a representative (but not limiting) example of needle identification markers is Arabic numerals (natural numbers). Specifically, the numeral "1" may be assigned to correspond to the first needle 50, the numeral "2" may be assigned to correspond to the second needle 50, and so forth.

This however is not the only option, as the needle identification markers may be assigned to only some of the needles 50, such as just the even-numbered needles 50, or to only the needles 50 that are multiples of three or more, e.g., five. Also, the needle identification markers are not limited to being numerals, and may instead be various kinds of symbols, graphics, colors or the like.

Although not depicted in the drawings, identification markers identifying each needle 50 may also be assigned (needle self-identification markers). As shown in FIG. 3, different colors are assigned to the needles 50 as needle self-identification markers, either over the entire length of the needles 50 or just a portion of the length. Specifically, red is assigned to the first needle 50, yellow is assigned to the second needle 50, green is assigned to the third needle 50, blue is assigned to the fourth needle 50, and purple is assigned to the fifth needle 50. The coloring of the sixth and subsequent needles 50 may repeat the pattern of coloring of the first to fifth needles 50.

This is not the only option, however, and needle self-identification markers may be assigned to only some of the needles 50, such as just the even-numbered needles 50, or just the needles 50 that are multiples of three or more, e.g., five.

As shown in FIGS. 1 to 4, left and right insertion holes 42 are formed in the base 30. The insertion holes 42 allow communication between the opposing (vertically-extending) faces of the bases 30. The insertion holes 42 are preferably formed large enough to allow the user (e.g., a pathologist, a technician, etc. as defined above) to insert one or more fingers and/or thumb therethrough.

As shown in FIGS. 1 to 4, the needle spacer 60 extends the entire length of the needles 50 on the lower side of the base 30. The needle spacer 60 may be formed from a plastic material, such as a synthetic resin, although it could also be metal. The needle spacer 60 may have, e.g., a substantially square or rectangular cross section, and may be in the form of a bar extending perpendicularly to the plurality of needles 50 (that is, parallel to the base 30), but again other shapes are possible, e.g. curved, arched or angled. During a normal slicing operation, the needle spacer 60 extends at least substantially horizontally, i.e. substantially in parallel with the specimen 300 and the support surface 100.

As shown in FIGS. 2-4, holes 61 are formed in the needle spacer 60 at a spacing that corresponds to the spacing of the needles 50. The holes 50 may have cross section that generally conforms to the outer cross section or profile of the needles 50, although the cross section of the holes 61 may differ from the outer cross section or profile of the needles 50. In the present embodiment, the holes 61 have a circular cross section that corresponds to the needles 50. The needles 50 are inserted through the respective holes 61 such that the needles 50 can move or slide relative to the holes 61. Thus, the needle spacer 60 is capable of moving (sliding) in the lengthwise direction of the needles 50. The holes 61 are preferably sized small enough to prevent plastic (permanent) deformation of the needles 50 during a set up operation, but large enough so that the needle spacer 60 can easily slide or move along the needles 50 relative to the base 30.

Identification markers for identifying the needles 50 and/or the gaps between the needles 50 may also be provided on the needle spacer 60 so as to correspond to the needles 50 and/or to the gaps between the needles 50 (the gaps between adjacent needles 50). As was noted above, identification markers for identifying the gaps between the needles 50 will be called "gap identification markers" herein, while identification markers for identifying the needles 50 will be called "needle identification markers" herein.

As shown in FIGS. 2 and 3, gap identification markers 62 are also provided on the needle spacer 60 and will be called needle spacer gap identification markers 62 herein. The gap identification markers 62 are, e.g., Arabic numerals (natural numbers), and are assigned to the gaps between the needles 50 (all of the gaps). Specifically, the numeral "1" is assigned to correspond to the first gap (the gap between the first needle 50 and the second needle 50), the numeral "2" is assigned to correspond to the second gap (the gap between the second needle 50 and the third needle 50), and so forth.

This however is not the only option, as the gap identification markers (62) may be assigned to only some of the gaps, such as just the even-numbered gaps, or only the gaps that are multiples of three or more, e.g., five. Also, the gap identification markers (62) are not limited to being numerals, and may instead be various kinds of symbols, graphics, colors or the like.

Also, in this exemplary embodiment, the gap identification markers 62 are provided in both directions in the width direction of the needle spacer 60, using the plurality of holes 61 (the row thereof) in the needle spacer 60 as a reference. The gap identification markers 62 (natural numbers) on each side are provided such that the side with the plurality of holes 61 (the row thereof) is the upper side.

Although not depicted in the drawings, needle identification markers may also be assigned to the needle spacer 60, instead of the gap identification markers 62, or in addition to the gap identification markers 62. Again, a representative example of needle identification markers is Arabic numerals (natural numbers). Specifically, the numeral "1" may be assigned to correspond to the first needle 50, the numeral "2" assigned to correspond to the second needle 50, and so forth.

This however is not the only option, as the needle identification markers may be assigned to only some of the needles 50, such as just the even-numbered needles 50, or only the needles 50 that are multiples of three or more, e.g., five. Also, the needle identification markers are not limited to being numerals, and may instead be various kinds of symbols, graphics, colors or the like.

As shown in FIGS. 1-5, the manipulation member 70 is disposed on the upper side of the base 30. The manipulation member 70 may be made of a plastic material, e.g., a synthetic resin, or it may be, e.g., metallic or wood. In the present embodiment, the representative (but not limiting) manipulation member is in the form of a bar having a substantially square cross section, has substantially the same length as the base 30, and extends parallel to the base 30. Thus, the manipulation member 70 extends along the base 30, i.e. parallel thereto. Thus, during use, the extension direction of the manipulation member 70 will extend at least substantially horizontally. The manipulation member 70 may also be called, e.g., a handle, and may have any other shape, e.g., a shape that conforms to the shape of the base 30 and/or the needle spacer 60.

The manipulation member 70 is connected to the needle spacer 60 by a pair of linking bars 75, although one linking bar 75 may be sufficient in certain embodiments of the present teachings. As shown in FIGS. 1-4, two through-holes 35 are formed in the base 30. The through-holes 35 are formed at or near the respective terminal (axial) ends of the needle spacer 60, such that all of the needles 50 in the lengthwise direction of the base 30 are disposed between the two through-holes 35. The through-holes 35 extend parallel to the plurality of needles 50. The linking bars 75 may be formed from metal, plastic, wood, etc. and extend parallel to the plurality of needles 50.

During use, the linking bars 75 extend at least substantially vertically. The linking bars 75 pass through the base 30 (i.e. through the through-holes 35) and are movable or slidable along their lengthwise direction relative to the base 30. The lower ends of the linking bars 75 are respectively affixed at or to the terminal (axial) ends of the needle spacer 60, such that all of the holes 61 are located therebetween. The upper ends of the linking bars 75 are respectively affixed at, to or near the terminal (axial) ends of the manipulation member 70.

Since the pair of linking bars 75 rigidly connects the needle spacer 60 to the manipulation member 70, the manipulation member 70 and the needle spacer 60 are capable of moving (up and down) integrally (as one unit). Further, by moving the manipulation member 70 up and down between its lowermost and uppermost positions, the needle spacer 60 will simultaneously move up and down between its lowermost and uppermost positions.

Figure 5:
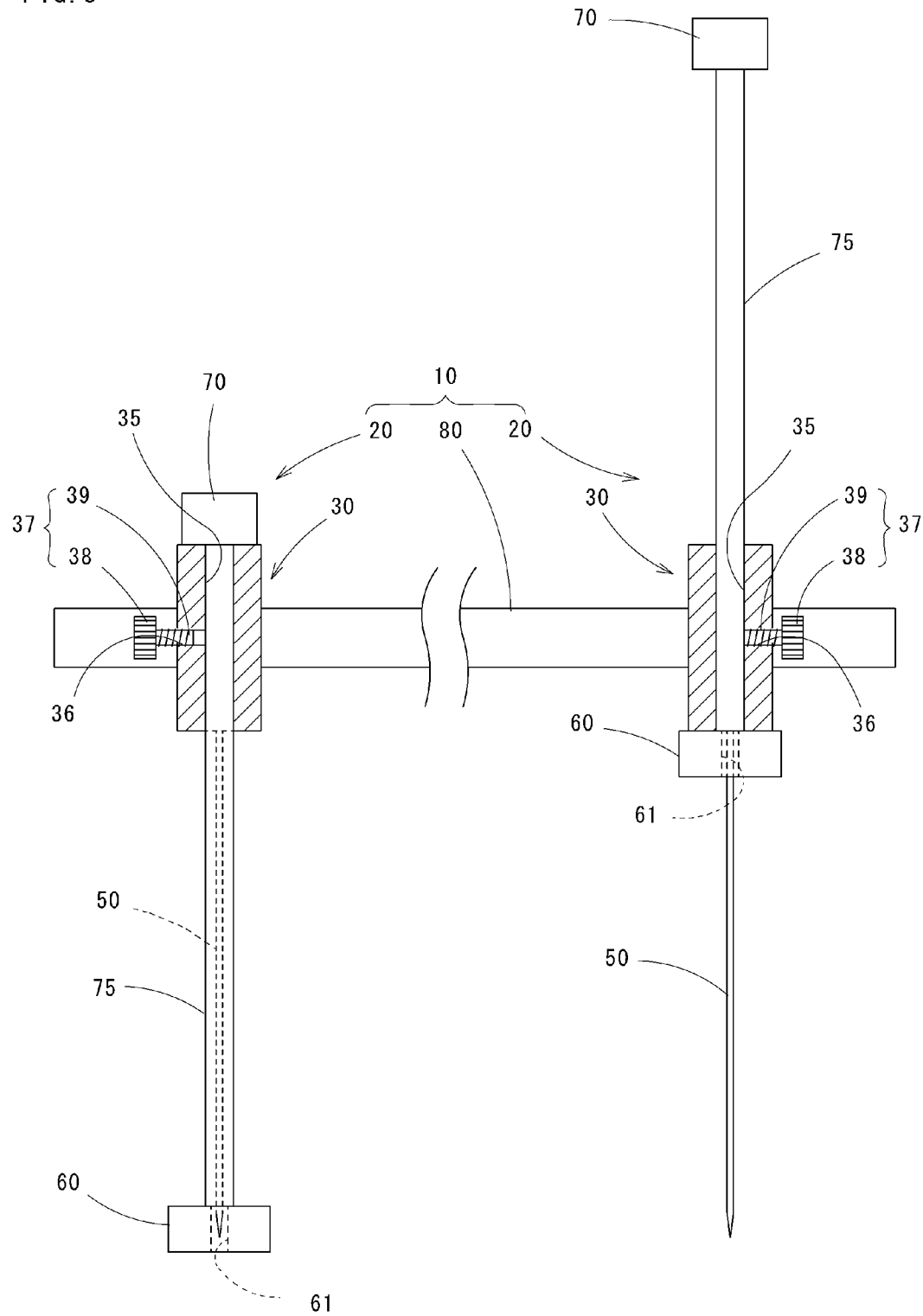
FIG. 5 is a detailed side view of the specimen slicing guide apparatus of FIG. 1, in which the needle spacer of one specimen slicing guide (left side) is located at its lowermost position (needle tip inclusion position), while the needle spacer of the other specimen slicing guide (right side) is located at its uppermost position.

As shown by the solid lines in FIG. 4, the lowermost position of the needle spacer 60 is the position at which the manipulation member 70 abuts or rests on the base 30. In FIGS. 1 and 5, the needle spacer 60 of the left specimen slicing guide 20 is located at its lowermost position. As shown by the two-dot chain lines in FIG. 4, the uppermost position of the needle spacer 60 is the position at which the needle spacer 60 contacts the base 30. In FIGS. 1 and 5, the needle spacer 60 of the right specimen slicing guide 20 is located at its uppermost position.

For the needle spacer 60, the position at which the distal (tip) ends of all of the needles 50 are located between the upper and lower edges of the needle spacer 60, i.e. the position at which the distal ends of all of the needles 50 are disposed within the thickness of the needle spacer 60 (the dimension in the vertical direction), will be called the "needle tip inclusion position". With this specimen slicing guide 20, the needle spacer 60 can move (descend) to the needle tip inclusion position as its lowermost position. The length of the pair of linking bars 75 is selected to achieve this relationship between the needle tips and the needle spacer 60.

The needle tip inclusion position may preferably be located anywhere within the height of the needle spacer 60 in the vertical direction, and in this exemplary embodiment, the height position in approximately middle of the range of the needle tip inclusion position is intended to be the lowermost position. Accordingly, in this exemplary embodiment, the needle spacer 60 can be located at the needle tip inclusion position not only at the lowermost position, but also when it is located near this position.

As shown in FIG. 5, threaded holes 36 are formed in the base 30 so as to be in communication with the through-holes 35. The threaded holes 36 respectively extend inwardly from the opposite sides of the bases 30 of the pair of specimen slicing guides 20 (which form the specimen slicing guide apparatus 10), all the way to the through-holes 35. Screws 37 are respectively provided in the threaded holes 36. The screws 37 each have a head 38 and a threaded shaft 39, and the shafts 39 mesh with the threaded holes 36. When the heads 38 are turned (rotated), the shafts 39 are caused to move toward or away from the linking bars 75 inside the threaded holes 36 (i.e. move between a non-pressing position and a pressing position as was described above).

As shown in the left specimen slicing guide 20 in FIG. 5, in the state in which the distal (tip) ends of the shafts 39 are not pressing against the linking bars 75 (i.e. when they are located at the non-pressing position), the linking bars 75 are permitted to slide within the through-holes 35. Therefore, the needle spacer 60 is permitted to move up and down together with the manipulation member 70 relative to the base 30. On the other hand, as shown in the right specimen slicing guide 20 in FIG. 5, in the state in which the distal ends of the shafts 39 are pressed against the linking bars 75 (i.e. when they are located at the pressing position), the linking bars 75 are prevented from sliding within the through-holes 35 relative to the base 30. Thus, the needle spacer 60 is prevented from moving up and down together with the manipulation member 70 relative to the base 30, and the needle spacer 60 is maintained or fixed at the desired height position (a position in the lengthwise direction of the plurality of needles 50) relative to the base 30 (and thus to the needles 50 as well).

In general, when not in use, the screws 37 may be tightened such that the manipulation member 70 and the needle spacer 60 are positioned at the needle tip inclusion position (the lowermost position or close to it), thereby covering or surrounding the sharp points of the needles 50.

As shown in FIGS. 1, 3 and 5, the specimen slicing guides 20 (the bases 30 thereof) are movably linked, and are held in spaced-apart parallel relationship, by the link 80. An integral specimen slicing guide apparatus 10 is thus formed from these three components. The link 80 is preferably linear in overall shape and has a uniform cross section (shape and size) along its lengthwise direction. Its shape may be, e.g., polygonal, such as triangular, square or rectangular, or may be partially curved, such as a semi-circle or arched. While a circular cross-section is also possible, it may be less advantageous than other shapes. An insertion hole 45 is formed in the base 30 of each of the specimen slicing guides 20. The shape and size of the insertion holes 45 correspond to the shape and size of the cross section of the link 80, so that the link 80 is not rotatable within the insertion holes 45 and thus is interference-fit or form-fit therein.

The link 80 is inserted into the respective insertion holes 45 of the specimen slicing guides 20 (bases 30) so as to be capable of moving or sliding along its lengthwise direction relative to the specimen slicing guides 20. Thus, the two specimen slicing guides 20 are coupled via the link 80 to form the specimen slicing guide apparatus 10.

Accordingly, the spacing or distance between the two specimen slicing guides 20 can be adjusted or changed by suitably sliding one or both of the specimen slicing guides 20 in the lengthwise direction of the link 80.

Retainers or stops, which are larger than the insertion holes 45, may be provided on, at or near both ends of the link 80 so as to prevent the link 80 from being removed from the guides 20. Also, the link 80 may include length markers or graduations in order to enable the user to determine the length of the spacing, e.g., in millimeters, between the two specimen slicing guides 20 (bases 30) and also to adjust the desired spacing with greater ease. The number of link 80 need not be one, and two or more may be used instead.

As shown in FIGS. 3 and 4, a recess 44 may be formed in each base 30 so as to be in communication with the insertion hole 45. The recess 44 extends downward from the upper surface of the base 30. A threaded hole 46 is formed in the recess 44 so as to extend from the recess 44 to the insertion hole 45. A screws 47 is threadably provided in the threaded hole 46. The screw 47 includes a head 48 and a threaded shaft 49, and the shaft 49 meshes with the threaded hole 46. When the head 48 is turned or rotated, the shaft 49 moves toward or away from the link 80 inside the threaded holes 46.

In the state in which the distal ends of the shafts 49 are pressed against the link 80, the link 80 is prevented from sliding inside the insertion holes 45, thereby fixing the bases 30 (specimen slicing guides 20) at desired positions on the link 80, thereby maintaining the bases 30 (specimen slicing guides 20) at the desired parallel spacing.

A recess 74 is also formed in the manipulation member 70 at a position corresponding to the screw 47 (in particular, to the head 48 thereof). The recess 74 is formed so as to extend upward from the lower surface of the manipulation member 70 in order to avoid interference between the manipulation member 70 and the screw 47 (head 48) when the manipulation member 70 is disposed in its lowermost (abutting) position.

At least the surface of the support 100 (FIG. 1) is formed from a pierceable material, such as e.g., polystyrene or polyurethane foam, a rubber material or a cork material. For example, the lower portion of the support 100 can be formed from another harder material to provide more structural strength to the support 100, such that only the upper or top portion (the portion on the upper side) is made, e.g., from polystyrene or polyurethane foam, a rubber material or a cork material. Since at least the top or upper surface of the support 100 is formed of a pierceable material, the needles 50 will be maintained (held) upright (at least substantially vertical) when the needles 50 (the distal ends thereof) have been stuck into (have pierced) the surface of the support 100. As used herein, the term "pierceable material" means that the material can be penetrated by the sharp end of a needle 50 by pressing using a force easily apply by a human. The pierceable material may be an elastomeric compound.

Next, a representative (not limiting) method for using the representative specimen slicing guide apparatus 10 (specimen slicing guides 20), as well as its operation and effects, will be described in the following. While the method described in the following generally refers to the specimen slicing guide apparatus 10, it should be understood that a single specimen slicing guide 20 may be used in substantially the same manner.

Before slicing a specimen 300 (FIGS. 7A and 7B), the user will set up the specimen slicing guide apparatus 10 (the two specimen slicing guides 20). A representative method for setting up this specimen slicing guide apparatus 10 (specimen slicing guides 20) will be described with reference to FIGS. 6A to 6D, etc.

Figure 6A:
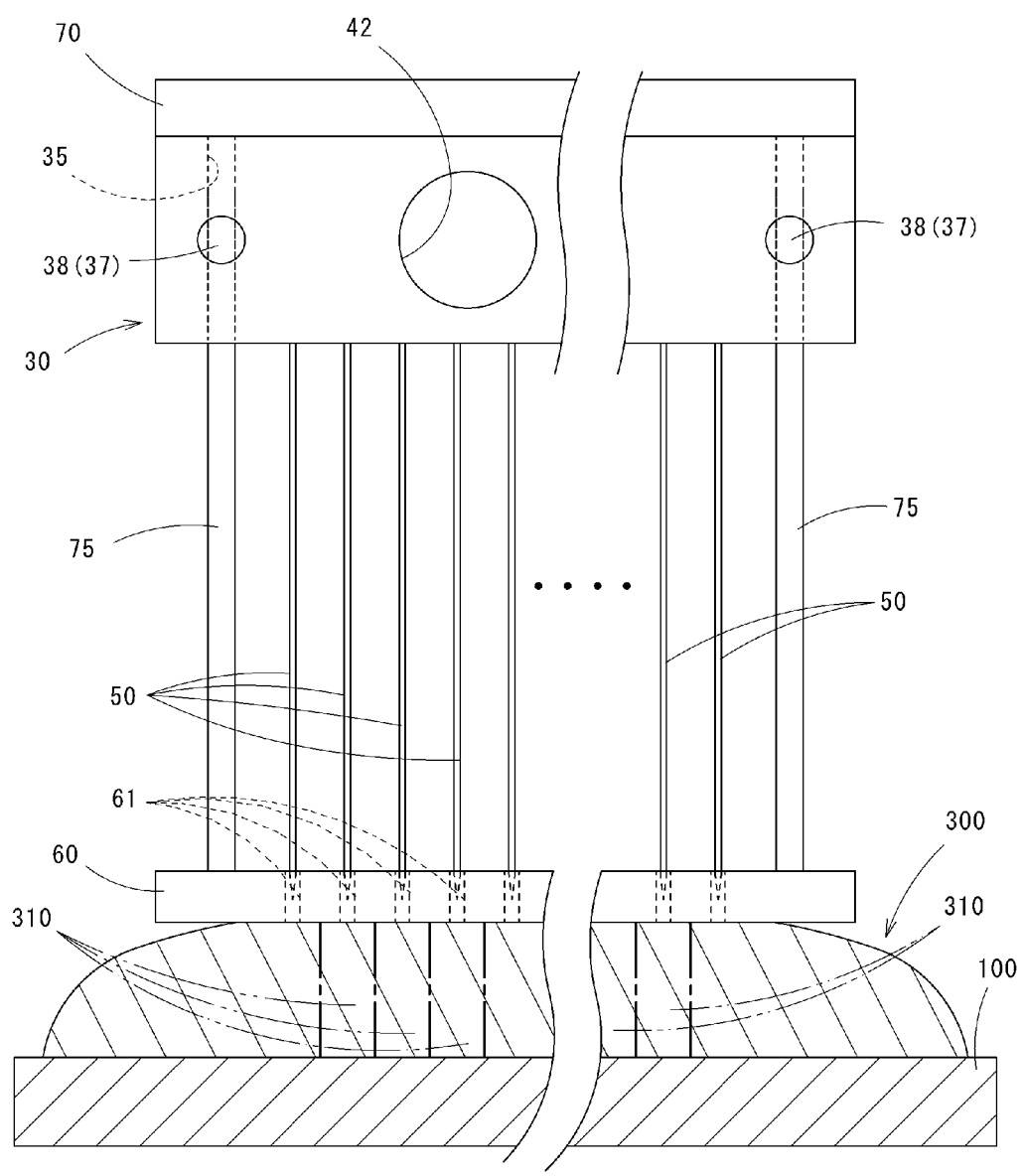
FIG. 6A is a diagram for illustrating a method of using (set-up/separation method) one specimen slicing guide of FIG. 1.

As shown in FIG. 7A, first the user places the specimen 300 on the support surface 100 (see FIG. 6A as well). The user may also adjust the spacing between the two specimen slicing guides 20 of the specimen slicing guide apparatus 10 in accordance with the size of the specimen 300 to be sliced. For example, if the specimen 300 is large, the specimen slicing guides 20 may be spaced farther apart, whereas if the specimen 300 is small, the specimen slicing guides 20 may be spaced closer together.

Then, as shown in FIG. 6A, the user loosens the screws 37 of each of the specimen slicing guides 20 (see the left specimen slicing guide 20 in FIG. 5), which enables the needle spacer 60 to able to move up and down relative to the base 30. At this time, the needle spacer 60 is preferably positioned at the needle tip inclusion position (lowermost position). As was noted above, the needle spacer 60 is preferably normally positioned at the needle tip inclusion position when not in use.

Then, as shown in FIG. 6A, the user positions the specimen slicing guides 20 so that the needle spacers 60 abut or rest on the specimen 300 (the upper surface thereof).

Figure 6B:
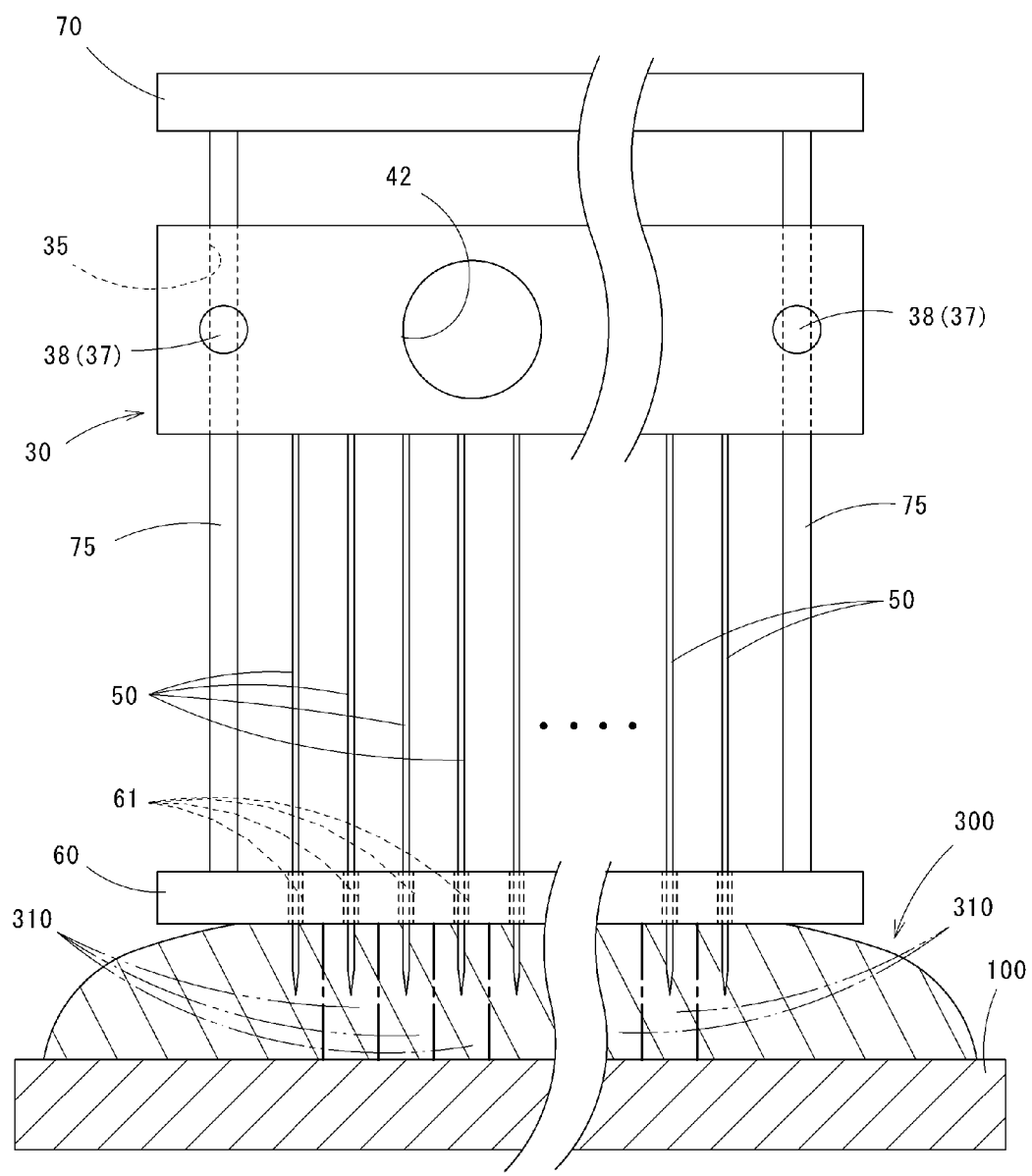
FIG. 6B is another diagram for illustrating the method of using (set-up/separation method) the specimen slicing guide of FIG. 1, and shows a state either before (separation) or after (set-up) the state shown in FIG. 6A.

Then, as shown by considering FIG. 6A→FIG. 6B as a time sequence, the user lowers the bases 30 while maintaining the manipulation members 70 and the needle spacers 60 at least substantially stationary. Consequently, the needles 50 descend relative to the needle spacers 60 and the needles 50 (the distal ends thereof) penetrate into the specimen 300. This specimen piercing operation can be easily performed if the user inserts his/her thumbs or one or more fingers of the left and right hands into the respective insertion holes 42 of the bases 30 and presses the bases 30 downward by applying a downward force to the insertion holes 42. In the alternative, the user could press the link 80 downward (see FIG. 7A). As a result of these actions, the needle spacers 60, the manipulation member 70, etc., remain at least substantially stationary at their respective height positions, but rise relative to the needles 50 and the bases 30.

Figure 6C:
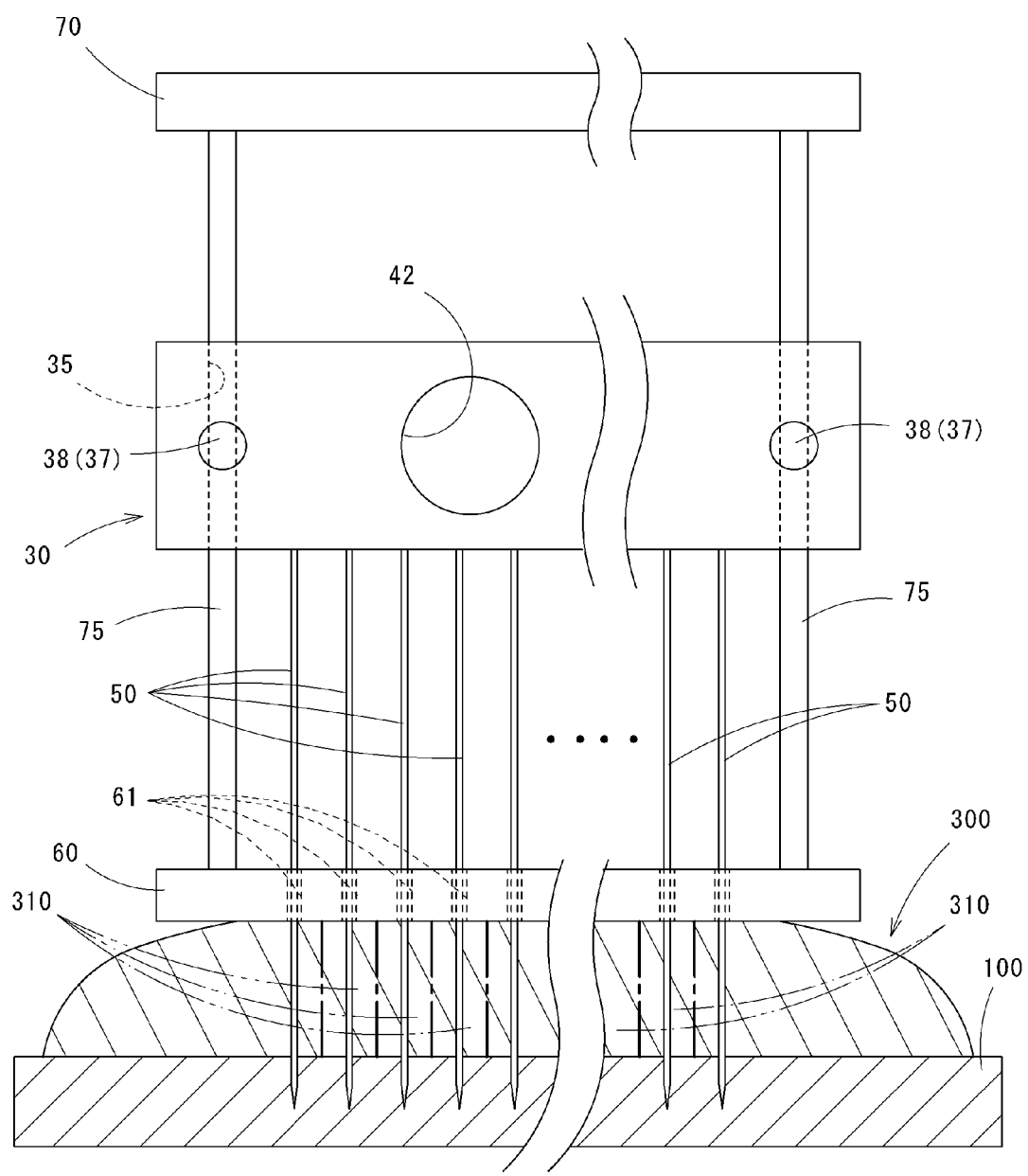
FIG. 6C is another diagram for illustrating the method of using (set-up/separation method) one specimen slicing guide of FIG. 1, and shows a state either before (separation) or after (set-up) the state shown in FIG. 6B.

As shown by considering FIG. 6B→FIG. 6C as a time sequence, when the above-described relative movement further proceeds, the needles 50 pass through the specimen 300, and the needles 50 (the distal ends thereof) penetrate (pierce) into the support surface 100. Consequently, the needles 50 will be held by the support 100, and the specimen slicing guides 20 (the specimen slicing guide apparatus 10) will be fixed to the support 100 at their respective positions, together with the specimen 300.

Figure 6D:
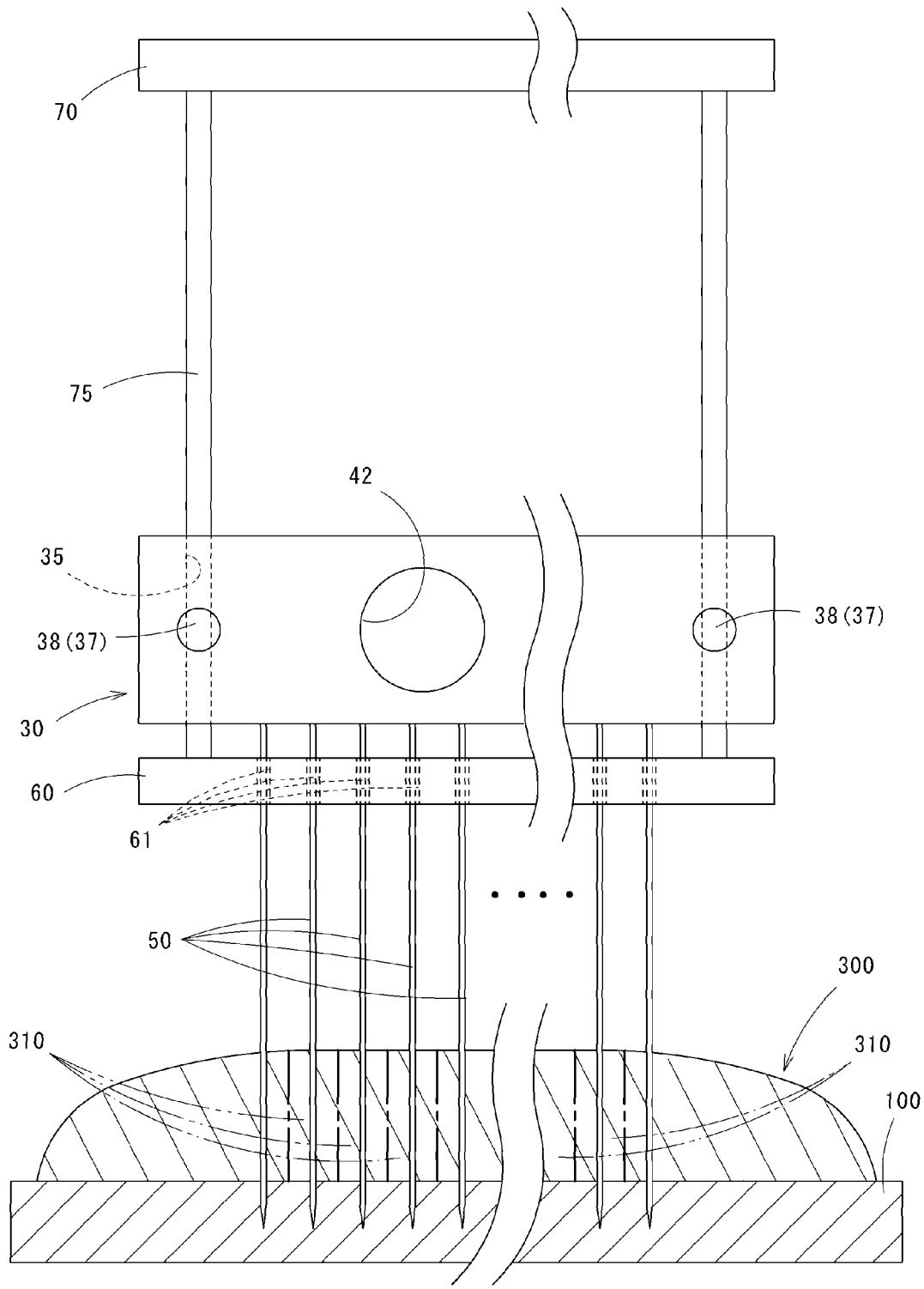
FIG. 6D is another diagram for illustrating the method of using (set-up/separation method) one specimen slicing guide of FIG. 1, and shows a state either before (separation) or after (set-up) the state shown in FIG. 6C.

Then, as shown by considering FIG. 6C→FIG. 6D as a time sequence, the user raises the manipulation member 70 of each of the specimen slicing guides 20. Consequently, the needle spacers 60 rise along with the manipulation members 70. When the needle spacers 60 have been raised sufficiently higher than the specimen 300, the user tightens the screws 37 (see the right specimen slicing guide 20 in FIG. 5). The needle spacers 60 are thus maintained at a position that is sufficiently higher than the specimen 300 so they will not get in the way of (interfere with) the slicing work to be done by the user, as will be discussed further below. Thus, as shown in FIG. 7A, the blade 210 of the knife 200 can be inserted into the gaps between the needles 50 of the corresponding specimen slicing guides 20 at a height position that is lower than the needle spacers 60 without interference therefrom. The needle spacers 60 may then be maintained at this height position during the slicing of the specimen 300.

Next, the user slices the specimen 300. A representative slicing method will now be described with reference to FIGS.

7A and 7B. First, as shown by the solid lines→one-dot chain lines in FIGS. 7A and 7B, the user inserts the knife 200 (the blade 210 thereof) into one gap between adjacent needles 50 of one of the specimen slicing guides 20 and then into a corresponding gap between adjacent needles 50 of the other specimen slicing guide 20. Then, as shown by the one-dot chain lines→two-dot chain lines in FIG. 7A, the knife 200 is lowered in this inserted state, so that the specimen 300 is cut by the blade 210. The slicing work may then be performed sequentially starting from the gaps on one side of the specimen slicing guides 20 to the gaps on the other side. A plurality of slices 310 of the specimen 300 are thus made.

The above-described slicing operation will be described in further detail with reference to FIGS. 3, 7A, and 7B. Specifically, the user first inserts the blade 210 of the knife 200 into the space (first paired gap formation space) formed by a first gap of one of the specimen slicing guides 20 (a gap between adjacent needles 50) and a first gap of the other specimen slicing guide 20. In this case, as shown in FIG. 7B, a visual guide is provided by the gap identification marker 62 ("1") on the user's side of the needle spacer 60 of one of the blade specimen slicing guides 20, and another visual guide is provided by the gap identification marker 62 ("1") on the user's side of the needle spacer 60 of the other specimen slicing guide 20.

Optionally, an assistant of the user may be located on the opposite side from the user with the specimen slicing guide apparatus 10 in between them. In the present embodiment, the assistant also has a visual guide, because the gap identification marker 62 ("1") is also provided on the assistant's side on the needle spacer 60 of one of the specimen slicing guides 20 as well as on the assistant's side on the needle spacer 60 of the other specimen slicing guide 20.

Also, as shown in FIG. 3, the user and the assistant can use as a visual guide "red" as the needle identification marker of the first needle 50 of one of the specimen slicing guides 20 and "yellow" as the needle identification marker of the second needle 50, and can use as a visual guide "red" as the needle identification marker of the first needle 50 of the other specimen slicing guide 20 and "yellow" as the needle identification marker of the second needle 50.

Thus, the user (and the assistant) can insert the blade 210 of the knife 200 into the first paired gap formation space while using the respective needle spacer gap identification markers 62 and the needle self-identification markers as visual guides. In the above procedure, the user and/or the assistant may use the gap identification markers 32 (base gap identification markers) 32 provided on the base 30 (FIG. 3) along with, or instead of, the gap identification markers (needle spacer gap identification markers) 62 provided on the needle spacer 60.

Next, the user lowers the knife 200 in this inserted state to cut the specimen 300. Specifically, the blade 210 of the knife 200 is guided by the two pairs of needles 50 constituting the first paired gap formation space while the knife 200 is lowered to make a cut.

Then, in the same manner as discussed above, the user inserts the blade 210 of the knife 200 into an adjacent space (second paired gap formation space) formed by the second gap of one of the specimen slicing guides 20 and the second gap of the other specimen slicing guide 20, and lowers the knife 200 in this state (guided state) to cut the specimen 300. The above procedure is repeated to cut the specimen 300 into a plurality of slices 310 corresponding to the gaps between the needles 50.

In addition to slicing at every gap, slices may also be made by cutting only at even-numbered gaps, such as the second gap, fourth gap, sixth gap, and so on (that is, a slice may be made at every other gap), or only at gaps with numbers that are multiples of three or more, such as the third gap, the sixth gap, the ninth gap, and so on (that is, a slice may be made at every third gap).

After the specimen 300 has been sliced as described above, the specimen slicing guide apparatus 10 (the specimen slicing guides 20) is then separated from the specimen 300 (all of the slices 310) and the support surface 100. A representative method for separating the specimen slicing guide apparatus 10 (the specimen slicing guides 20) will be described with reference to FIGS. 6A to 6D.

First, the user loosens the screws 37 (see the left specimen slicing guide 20 in FIG. 5), and then presses the manipulation member 70 of each specimen slicing guide 20 downward to lower it as far as it will go, as shown by considering FIG. 6D→FIG. 6C as a time sequence. Consequently, the two needle spacers 60 descend until they abut or rest on the specimen 300 (the upper surface thereof).

Next, as shown by considering FIG. 6C→FIG. 6B as a time sequence, the user presses the manipulation members 70 downward while urging or pressing the bases 30 upward, i.e. the manipulation members 70 are moved closer to the bases 30. Consequently, the needle spacers 60 press downward on the specimen 300 and, as a result, the bases 30 and the needles 50 rise relative to the specimen 300. More specifically, when the manipulation members 70 are pressed downward, the pressing force is transmitted via the pair of linking bars 75 to the needle spacers 60, and the needle spacers 60 press the specimen 300 (i.e. the set of slices 310) downward. This pressing force prevents the specimen 300 and the support surface 100 from rising. At the same time, the bases 30 are urged or moved upward relative to the specimen 300, thereby causing the needles 50 to rise along with the bases 30. Consequently, all of the needles 50 rise against the frictional force acting between the needles 50 and the specimen 300 (the slices 310) and the support surface 100.

Thus, the slicing guides 20 can easily be separated from the specimen 300 by downwardly pressing the upper edges of the manipulation members 70 using thumbs or one or more fingers of the left and right hands. For example, the thumbs or one or more fingers of the left and right hands can be inserted into the respective insertion holes 42 of the bases 30, in order to use the thumbs or other fingers to urge or press the bases 30 upward.

As shown by considering FIG. 6B→FIG. 6A as a time sequence, when the bases 30 move closer to the manipulation members 70 while maintaining pressure on the specimen slices 310 via the needle spacer 60, the needles 50 withdraw from the specimen 300 (specimen slices 310). More specifically, at the point when the needle spacers 60 approach the lowermost position and the distal ends of all of the needles 50 are at the same height as the lower edges of the needle spacers 60 (the same height as the upper face of the specimen 300), all of the needles 50 come out of the specimen 300 (the slices 310). As a result, the specimen slicing guide apparatus 10 (specimen slicing guides 20) separates from the specimen 300.

Thereafter, as shown in FIG. 4, the screws 37 may be tightened while the needle spacers 60 are located at the needle tip inclusion position (the lowermost position or close to it), thereby maintaining or fixing the needle spacers 60 at the needle tip inclusion position (the lowermost position or close to it), thereby concluding the work of slicing of the specimen 300 using the specimen slicing guide apparatus 10 (specimen slicing guides 20).

After the specimen 300 has been sliced as discussed above (i.e., in the state immediately after slicing), cuts are present in the specimen 300, but the specimen 300 generally retains the same overall shape as it had before being sliced. Consequently, after the slicing has been completed, it is possible to easily assign position information to the slices 310 (information indicating where the slices 310 were located in the state prior to the slicing of the specimen 300), such as assigning numbers to the slices 310.

After position information has thus been assigned to the slices 310, the slices 310 are separated from one another and the slices 310 may be subjected to subsequent processing for further analysis and diagnosis. The analysis results are combined with the position information for the slices 310, which clarifies the distribution of lesion across the entire specimen 300 and enables a pathological diagnosis.

As discussed above, by using this specimen slicing guide apparatus 10 (see FIG. 7A, etc.), the specimen 300 (to be sliced) can be easily fixed to the support surface 100 using the plurality of needles 50 of the two specimen slicing guides 20. In addition, the specimen slicing guides 20 themselves can be easily fixed (set up) on the support surface 100 by the needles 50 of each guide 20.

Further, after the specimen 300 and the specimen slicing guides 20 have been fixed to the support surface 100, the blade 210 of the knife 200 can be inserted into a specific paired gap formation space, and the knife 200 can be lowered while being guided by the two pairs of needles 50. Therefore, the specimen 300 can be cut substantially vertically (along the direction of the two pairs of needles 50) and into uniformly spaced apart slices 310. Thus, the specimen 300 can be uniformly sliced using the specimen slicing guide apparatus 10, such that the thickness of each of the slices 310 will be the same at all locations, and the thickness of all the slices 310 will also be the same.

Furthermore, in the specimen slicing guide apparatus 10 as described above, the gap identification markers 62 are assigned to the needle spacers 60 of both of the specimen slicing guides 20 (see FIGS. 2 and 7B, etc.), the gap identification markers 32 are assigned to the bases 30 (see FIGS. 2 and 3), and the needle self-identification markers (coloring for identifying the needles themselves) are assigned to the needles 50 of the specimen slicing guides 20 (see FIG. 3). As a result, the user can easily insert the knife 200 into the corresponding gap of the needles 50 between the specimen slicing guides 20 (paired gap formation space) by using the gap identification markers 62 and 32 and the needle self-identification markers as visual guides. Thus, the specimen 300 can be easily and properly sliced by using this specimen slicing guide apparatus 10.

Since the needle spacers 60 are closer to the specimen 300 and at a position that is lower than the position of the bases 30, the user may prefer to use the gap identification markers provided on the needle spacers 60 (needle spacer gap identification markers) 62 as the visual guide, rather than using the gap identification markers provided on the bases 30 (base gap identification markers) 32 as the visual guide. Also, the needle spacers 60 are maintained at a position that is sufficiently higher than the specimen 300 to avoid interference with the slicing work, but the user may prefer to set the needle spacer 60 at the lowest position that still allows the above-mentioned slicing work to be carried out without inconvenience.

Moreover, the present specimen slicing guides 20 (specimen slicing guide apparatus 10) enable the needle spacers 60 to move up and down along the needles 50 while the needles 50 are inserted in the holes 61 in the needle spacers 60. In addition, it is also possible to lower the needle spacer 60 to the needle tip inclusion position as the lowermost position (see FIGS. 6A to 6D, etc.), so that the following action and effect result. In particular, the needles 50 will be subjected to an impact force when the needles 50 are stuck into the specimen 300 and pass through (pierce or penetrate) the specimen 300. However, by using the present specimen slicing guides 20, throughout the entire process of pressing the needles 50 through the specimen 300, the portions of all the needles 50 adjacent to the upper surface of the specimen 300 are maintained in a uniformly spaced apart state in the lateral direction by the needle spacers 60. That is, this portion of all the needles 50 is limited to or maintained at a spacing that corresponds to the spacing of the holes 61 in the needle spacers 60. Therefore, when the specimen slicing guides 20 are set up (when the needles 50 are stuck into and pass through the specimen 300), the needles 50 are prevented from being bent by the resulting impact force, and all of the needles 50 are reliably and uniformly maintained in a parallel state.

Also, as discussed above, when the needles 50 have been inserted into the holes 61 of the needle spacers 60 of the present specimen slicing guides 20 (specimen slicing guide apparatus 10), the needle spacers 60 are capable of moving up and down along (relative to) the needles 50, and are capable of being lowered to the needle tip inclusion position as the lowermost position (see FIGS. 6A to 6D, etc.). Therefore, the following action and effect result. That is, the work of slicing the specimen 300 using the specimen slicing guide apparatus 10 (specimen slicing guide 20) is carried out with the plurality of needles 50 passed through the specimen 300 and stuck into the support surface 100. After the slicing work is finished, the specimen slicing guides 20 (specimen slicing guide apparatus 10) must be separated from the specimen 300 (all of the slices 310) and the support surface 100 (this was discussed above).

However, since the specimen 300 (the slices 310) and the support surface 100 will usually stick or adhere to the needles 50, when it is attempted to separate the specimen slicing guides 20 (specimen slicing guide apparatus 10) from the specimen 300 and the support surface 100 (that is, if an attempt is made to remove all the needles 50 from the specimen 300 and the support surface 100), a frictional force will be exerted between the needles 50 and the support surface 100 and the specimen 300 (slices 310). That is, if it is attempted to pull the needles 50 out of the support surface 100 and the specimen 300 in order to raise the needles 50 (the specimen slicing guides 20), the specimen 300, etc., may also rise along with the needles 50.

However, by pressing downward on the manipulation members 70 of the specimen slicing guides 20 (specimen slicing guide apparatus 10) at this time, the needle spacers 60 will press the specimen 300 (the group of slices 310) downward and prevent the specimen 300, etc., from rising. At the same time, the bases 30 are forced or urged upward relative to the needle spacers 60, so that the needles 50 rise along with the bases 30. Therefore, all of the needles 50 rise against the frictional force exerted between the needles 50 and the specimen 300 (slices 310) and the support surface 100, and can be pulled out of the support surface 100 and the specimen 300. Consequently, the specimen slicing guides 20 (specimen slicing guide apparatus 10) can be easily separated from the specimen 300 and the support surface 100 without moving or altering the relative positions of the specimen slices 310.

As was described above, if the insertion holes 42 are defined in the bases 30 of the specimen slicing guides 20, the user can perform the work of separating the specimen slicing guides 20 from the specimen 300 (specimen slices 310) by pressing down on the upper edges of the manipulation members 70 and using a thumb or finger inserted into each insertion hole 42 of the base 30 to pull the base 30 upwardly. This allows the user to easily move the bases 30 upward relative to the specimen 300. Therefore, the separation can be easily carried out by the manual action of bringing the finger(s), which are pressing on the upper edge of the manipulation member 70, closer to the finger(s) inserted into the insertion holes 42.

Moreover, since the needle spacers 60 can be fixed and maintained in the needle tip inclusion position as the lowermost position when not in use (see e.g., FIG. 4) by tightening the screws 37 with the needle spacers 60 located at the needle tip inclusion position, i.e. at their lowermost position, the distal ends of the needles 50 are will be covered by the interior of the needle spacers 60 (between the upper and lower edges). This prevents the distal ends of the needles 50 from being exposed, which improves safety.

In other words, the specimen slicing guides 20 may be designed so that the needle spacers 60 are only able to descend to the needle tip inclusion position as their lowermost position (see FIG. 4, etc.). Therefore, the needle spacers 60 are prevented from separating from the needles 50. As a result, it can be avoided that the needles 50 come out of the needle spacers 60, which would require the needles 50 to be re-inserted into the holes 61 in the needle spacers 60, thereby requiring the plurality of needles 50 to be simultaneously inserted into the holes 61 in the needle spacers 60, which can be difficult. That is, the present specimen slicing guides 20 (specimen slicing guide apparatus 10) prevent the needles 50 from coming out of the needle spacers 60 (the needle spacers 60 are prevented from separating from the needles 50), thereby avoiding the need to perform this difficult job.

Because of this, with these specimen slicing guides 20, when it is attempted to lower the needle spacers 60 to the needle tip inclusion position (lowermost position), there is no need to use a special (additional) device to prevent the needle spacers 60 from coming out of the needles 50, and the needle spacers 60 can be easily lowered to the needle tip inclusion position.

It should be understood that the above-description concerns merely a representative embodiment for practicing the present invention and a wide variety of modifications can be made based upon the knowledge of a person skilled in the art.

For example, it is not necessary to provide the gap identification markers (32, 62) on one or both of the bases 30 and the needle spacers 60. Also, it is not necessary to provide both the gap identification markers (32, 62) and the needle self-identification markers. Just one may be sufficient in certain aspects of the present teachings.

Also, the needle spacers (60) are not required to descend all the way to the needle tip inclusion position as their lowermost position, and instead may be designed to only descend to a position above it.

Furthermore, instead of providing a single specimen slicing guide apparatus (10) formed by linking a pair of specimen slicing guides (20) using a link (80), a pair of specimen slicing guides (20) may be used independently. In this case, the user may set up the pair of specimen slicing guides (20) by putting them opposite one another without a link therebetween.

The invention claimed is:

1. A specimen slicing guide configured to assist in slicing a specimen taken from a human or an animal, comprising:
    a base extending in an extension direction having a horizontal component;
    a plurality of needles extending from the base with gaps provided between the needles in the extension direction of the base, the needles extending at least substantially parallel to each other and at least substantially perpendicular to the horizontal component of base;
    a needle spacer having a plurality of holes, the plurality of needles being respectively disposed in the plurality of holes and the needle spacer being configured to press against the specimen and to move relative to the base;
    a manipulation member extending along an upper side of the base opposite of the needle spacer and being movable relative to the base; and
    at least one linking bar that is movable relative to the base, wherein:
    a first portion of the linking bar is connected to the manipulation member and is disposed on one side of the base and
    a second portion of the linking bar is connected to the needle spacer and is disposed on the opposite side of the base.

2. The specimen slicing guide according to claim 1, wherein at least first and second linking bars extend at least partially through the base and connect the manipulation member to the needle spacer, and wherein the first and second linking bars extend in parallel to the plurality of needles with the plurality of needles being disposed therebetween.

3. The specimen slicing guide according to claim 2, wherein the needle spacer is configured to be moved to a needle tip inclusion position at which distal ends of the plurality of needles are located between upper and lower edges of the needle spacer, the needle tip inclusion position being the farthest-most position, to which the needle spacer is permitted to move away from the base.

4. The specimen slicing guide according to claim 3, wherein the manipulation member is configured to abut on the base when the needle spacer is disposed at its lowermost position.

5. The specimen slicing guide according to claim 4, further comprising at least one insertion hole defined in the base and sized to receive a human finger or thumb.

6. The specimen slicing guide according to claim 5, further comprising a fixing mechanism configured to releasably fix the needle spacer relative to the needles and to prevent movement of the needle spacer along a lengthwise direction of the needles relative to the base.

7. The specimen slicing guide according to claim 6, wherein the fixing mechanism includes:
    at least one threaded hole disposed in the base adjacent to at least one linking bar, and
    at least one screw threadably disposed in the at least one threaded hole, the at least one screw being configured move between a pressing position, at which the screw is pressed against the linking bar, and a non-pressing position, at which the screw is not pressed against the linking bars.

8. The specimen slicing guide according to claim 7, further comprising gap identification markers on the needle spacer, the gap identification markers identifying respective gaps between adjacent needles.

9. The specimen slicing guide according to claim 8, wherein the gap identification markers are provided on both sides in a width direction of the needle spacer.

10. The specimen slicing guide according to claim 9, wherein the needles are equally spaced apart in a linear row at intervals between 2-4 millimeters, the needles are resiliently bendable, the needles have a rounded outer profile corresponding to an inner cross section of the holes of the needle spacer, and the needle spacer has a flat side configured to abut against the specimen.

11. The specimen slicing guide according to claim 1, wherein the needle spacer is configured to be moved to a needle tip inclusion position at which distal ends of the plurality of needles are located between upper and lower edges of the needle spacer, the needle tip inclusion position being the farthest-most position, to which the needle spacer is permitted to move away from the base.

12. The specimen slicing guide according to claim 11, wherein the manipulation member is configured to abut on the base when the needle spacer is disposed at its lowermost position.

13. The specimen slicing guide according claim 1, further comprising at least one insertion hole defined in the base and sized to receive a human finger or thumb.

14. The specimen slicing guide according to claim 1, further comprising a fixing mechanism configured to releasably fix the needle spacer relative to the needles and to prevent movement of the needle spacer along a lengthwise direction of the needles relative to the base.

15. The specimen slicing guide according to claim 14, wherein the fixing mechanism includes:
   at least one threaded hole disposed in the base adjacent to at least one linking bar, and
   at least one screw threadably disposed in the at least one threaded hole, the at least one screw being configured move between a pressing position, at which the screw is pressed against the linking bar, and a non-pressing position, at which the screw is not pressed against the linking bars.

16. A specimen slicing guide apparatus, the apparatus comprising:
   two specimen slicing guides according to claim 1; and
   a link configured to adjustably retain the two specimen slicing guides in a spaced-apart, parallel relationship.

17. A method for slicing a specimen taken from a human or an animal, comprising:
   placing the needle spacer of the specimen slicing guide of claim 1 on an upper surface of the specimen,
   pushing at least some of the needles of the specimen slicing guide through the specimen and into a support surface while the needle spacer is maintained at or near the upper surface of the specimen, thereby fixing the needles in the support surface relative to the specimen,
   slicing the specimen using gaps between adjacent needles as a guide for a knife, and
   removing the needles from the sliced specimen by upwardly moving the needles away from the sliced specimen and support surface while the needle spacer is maintained at the upper surface of the specimen.

18. The method according to claim 17, wherein the needle spacer is maintained at the upper surface of the specimen by pressing down on a manipulation member connected to the needle spacer via at least one linking bar, and the method further comprises after the pushing step but before the slicing step:
   moving the needle spacer away from the specimen and
   releasably fixing the needle spacer relative to the needles while the needle spacer is disposed at a position spaced from the specimen.

19. A specimen slicing guide configured to assist in slicing a specimen taken from a human or an animal, comprising:
   a base extending in an extension direction having a horizontal component;
   a plurality of needles extending from the base with gaps provided between the needles in the extension direction of the base, the needles extending at least substantially parallel to each other and at least substantially perpendicular to the horizontal component of base;
   a needle spacer having a plurality of holes, the plurality of needles being respectively disposed in the plurality of holes and the needle spacer being configured to press against the specimen and to move relative to the base; and
   at least one insertion hole defined in the base and sized to receive a human finger or thumb.

20. A specimen slicing guide configured to assist in slicing a specimen taken from a human or an animal, comprising:
   a base extending in an extension direction having a horizontal component;
   a plurality of needles extending from the base with gaps provided between the needles in the extension direction of the base, the needles extending at least substantially parallel to each other and at least substantially perpendicular to the horizontal component of base;
   a needle spacer having a plurality of holes, the plurality of needles being respectively disposed in the plurality of holes and the needle spacer being configured to press against the specimen and to move relative to the base; and
   a fixing mechanism configured to releasably fix the needle spacer relative to the needles and to prevent movement of the needle spacer along a lengthwise direction of the needles relative to the base.

* * * * *